US006923969B2

(12) United States Patent
Widjojoatmodjo et al.

(10) Patent No.: US 6,923,969 B2
(45) Date of Patent: Aug. 2, 2005

(54) NON-SPREADING PESTIVIRUS

(75) Inventors: Myra N. Widjojoatmodjo, Utrecht (NL); Robertus Jacobus Maria Moormann, Dronten (NL); Petrus Antonius Van Rijn, Lelystad (NL)

(73) Assignee: ID-Lelystad, Instituut voor Dierhouderij en Diergezondheid B.V., Lelystad (NL)

( * ) Notice: Subject to any disclaimer, the term of this patent is extended or adjusted under 35 U.S.C. 154(b) by 96 days.

(21) Appl. No.: 09/948,966

(22) Filed: Sep. 7, 2001

(65) Prior Publication Data

US 2002/0106641 A1 Aug. 8, 2002

Related U.S. Application Data

(63) Continuation of application No. PCT/NL00/00153, filed on Mar. 8, 2000.

(30) Foreign Application Priority Data

Mar. 8, 1999 (EP) .............................................. 99200669

(51) Int. Cl.$^7$ ...................... A61K 39/12; A61K 39/187; C12N 7/04; C12N 15/40; C12N 5/10
(52) U.S. Cl. ................................. 424/205.1; 424/218.1; 424/199.1; 435/235.1; 435/236; 435/320.1; 435/325; 536/23.72
(58) Field of Search .................... 536/23.72; 435/235.1, 435/236, 5, 320.1, 325; 424/199.1, 218.1, 205.1

(56) References Cited

U.S. PATENT DOCUMENTS

| 5,792,462 | A | * | 8/1998 | Johnston et al. | ......... | 424/199.1 |
| 6,033,886 | A | * | 3/2000 | Conzelmann | ............ | 435/235.1 |
| 6,168,942 | B1 | * | 1/2001 | Cao et al. | .................... | 435/236 |
| 6,242,259 | B1 | * | 6/2001 | Polo et al. | .................. | 435/456 |
| 6,555,346 | B1 | | 4/2003 | Kretzdorn et al. | | |

FOREIGN PATENT DOCUMENTS

| EP | 0 389 034 | 12/1990 |
| WO | WO 95/34380 | 6/1995 |
| WO | WO 96/19498 | 6/1996 |
| WO | WO 96/25496 | 8/1996 |
| WO | WO 99/31257 | 12/1998 |
| WO | 99/28487 | * 6/1999 ........... C12N/15/86 |

OTHER PUBLICATIONS

Moser et al (Journal of Virology 72(6): 5318–5322, Jun. 1998).*
Meyers et al (Journal of Virology 70(12): 8606–8613, 1996).*
Nettleton et al. British Veterinary Journal 151(6): 615–42, 1995 (abstract only cited).*
Khromykh et al (Journal of Virology 72:7270–7279, Sep. 1998).*
Lindenbach et al (Journal of Virology 71:9608–9617, Dec. 1997).*
Khromykhh et al (Journal of Virology 71:1497–1505, Feb. 1997).*
Meyers G. et al., "Classical Swine Fever Virus: Recovery of Infectious Viruses from cDNA Constructs and Generation of Recombinant Cytopathogenic Defective Interfering Particles," Journal of Virology, vol. 70, No. 3, pp. 1588–1595, Mar. 1996, American Soc. for Microbiology US.
Moormann R. J. M. et al., "Infectious RNA Transcribed from an Engineered Full–Length cDNA Template of the Genome of a Pestivirus," Journal of Virology, vol. 70, No. 2, pp. 763–770, Feb. 1996, American Soc. for Microbiology US.
Kuppermann H. et al., "Bovine Viral Diarrhea Virus: Characterization of a Cytopathogenic Defective Interfering Particle with Two Internal Delections," Journal of Virology, vol. 70, No. 11, pp. 8175–8181, Nov. 1996, American Soc. for Microbiology US.
PCT International Preliminary Examination Report, PCT/NL00/00153, dated Jun. 15, 2001.
Peeters B. et al., "Biologically safe, non–transmissible pseudorabies virus vector vaccine protects pigs against both Aujeszky's disease and classical swine fever," Journal of General Virology, vol. 78, pp. 3311–3115, 1997, GB.
van Rijn P.A. et al., "An experimental marker vaccine and accompanying serological diagnostic test both based on envelope glycoprotein E2 of classical swine fever virus (CSFV)," Vaccine 17, pp. 433–440, 1999, Deparment of Mammalian Virology, The Netherlands.
Moser, Christian, et al., "Detection of Antibodies Against Classical Swine Fever Virus in Swine Sera by Indirect ELISA Using Recombinant Envelope Glycoprotein E2," Veterinary Microbiology 51, pp. 41–53, 1996.
van Rijn, P.A. et al., "Classical Swine Fever Virus (CSFV) Envelope Glycoprotein E2 Containing One Structural Antigenic Unit Protects Pigs from Lethal CSFV Challenge," Journal of General Virology 77, pp. 2737–2745, 1996.
Hulst, M.M., et al., "Glycoprotein E1 of Hog Cholera Virus Expressed in Insect Cells Protects Swine from Hog Cholera," Journal of Virology, pp. 5435–5442, Sep. 1993.

(Continued)

*Primary Examiner*—Mary E. Mosher
(74) *Attorney, Agent, or Firm*—TraskBritt

(57) ABSTRACT

The invention relates to vaccines used in the eradication or control of pestivirus infections, particularly used in pigs or ruminants. The invention provides nucleic acid, pestivirus-like particles and a pestivirus vaccine, comprising the nucleic acid or particles, which is capable of eliciting a proper immune response without having the ability to spread throughout the vaccinated animal, thereby avoiding the negative consequences of viral spread. Preferably, the immunological response allows for serological discrimination between vaccinated animals and wild-type pestivirus infected animals.

8 Claims, 10 Drawing Sheets

OTHER PUBLICATIONS

Ruggli, Nicolas, et al., "Baculovirus Expression and Affinity Purification of Protein E1 of Classical Swine Fever Virus Strain Alfort/187," Virus Genes 10:2, pp. 115–126, 1995.

Hulst, Marcel M., et al., "Glycoprotein E2 of Classical Swine Fever Virus: Expression in Insect Cells and Identification as a Ribonuclease," Virology 200, pp. 558–565, 1994.

Kweon, Chang–Hee, et al., "Expression of Envelope Protein (E2) of Bovine Viral Diarrhea Virus in Insect Cells," J. Vet. Med. Sci. 59(5), pp. 415–419, 1997.

Reddy, J.R., et al., "Application of Recombinant Bovine Viral Proteins in the Diagnosis of Bovine Viral Diarrhea Infection in Cattle," Veterinary Microbiology 51, pp. 119–133, 1997.

Petric, Martin, et al., "Baculovirus Expression of Pestivirus Non–Structural Proteins," Journal of General Virology 73, pp. 1867–1871, 1992.

Chen, Liping, et al., "Coexpression of Cytochrome P4502A6 and Human NADPH–P450 Oxidoreductase in the Baculovirus System," Drug Metabolism and Disposition 25:4, pp. 399–405, 1997.

Radford, Kathryn M., et al., "The Indirect Effects of Multiplicity of Infection on Baculovirus Expressed Proteins in Insect Cells: Secreted and Non–Secreted Products," Cytotechnology 24, pp. 73–81, 1997.

Wu, Jianyong, et al., "Recombinant Protein Production in Insect Cell Cultures Infected with a Temperature–Sensitive Baculovirus," Cytotechnology 9, pp. 141–147, 1992.

Nguyen, Binh, et al., "Fed–Batch Culture of Insect Cells: A Method to Increase the Yield of Recombinant Human Nerve Growth Factor (rhNGF) in the Baculovirus Expression System," Journal of Biotechnology 31, pp. 205–217, 1993.

King, G., et al., "Assessment of Virus Production and Chloramphenicol Acetyl Transferase Expression of Insect Cells in Serum–Free and Serum–Supplemented Media Using a Temperature–Sensitive Baculovirus," Biotechnology and Engineering 38, pp. 1091–1099, Nov. 1991.

Khromykh et al., trans–Complementation of Flavivirus RNA Polymerase Gene NS5 by Using Kuhjin Virus Replicon–Expressing BKH Cells, Journal of Virology, Sep. 1998, pp. 7270–7279, vol. 72, No. 9.

Wong et al., Low Multiplicity Infection of Insect Cells with a Recombinant Baculovirus: The Cell Yield Concept, Biotechnology and Bioengineering, vol. 49, pp. 659–666 (1996).

Hulst et al., Classical swine fever virus diagnostics and vaccine production in insect cells, Cytotechnology, vol. 20, pp. 271–279, 1996.

* cited by examiner

Fig. 1

Characterization of recombinant viruses

| Schematic representation of recombinant E$^{rns}$ [a] | deletion or mutation [b] | virus | IPMA reactivity [c] SK6c26 b3 | IPMA reactivity [c] SK6 cells b3 | IPMA reactivity [c] SK6 cells R716 | IPMA reactivity [c] C5 | infectious virus recovered SK6c26 | infectious virus recovered SK6 cells |
|---|---|---|---|---|---|---|---|---|
| | none | Flc2 | + | + | + | + | + | + |
| | 422-488 | Flc22 | + | + | + | + | + | − |
| | 273-488 | Flc23 | + | + | − | − | + | − |
| | 422-436 | Flc30 | + | + | − | − | + | − |
| | 422 CYS→SER | Flc31 | + | + | − | − | + | − |
| | 405 CYS→SER | Flc32 | + | + | + | + | + | + |
| | 381 CYS→SER | Flc33 | + | + | − | − | + | − |

Fig. 3

Fig. 4 growth curve recombinant full lengths CSFV on SK6c26

TCID50/ml time in days

Fig. 5

Flc2
ENITQWNLSDNGTNFTGIQHAMYLRGVNRSLHGIWPGKICKGVPTHLATDVELKEIQGMMDASE
GTNYTCCKLQRFTHEWNKHGWCNWHNIDPWIQLMNRTQADLAEGPPVKECAVTCRYDKDADI
NVVTQARNRPFTTTLTGCKKGKNFSFAGTVIESPCNFNVSVEDTLYGDHECGSLLQDAALYLVDG
MTNTIEFTNARQGAARVTSWLGRQLRTAGKRLEGRSKTWFGAYA (SEQ ID NO:22)

Flc22
ENITQWNLSDNGTNFTGIQHAMYLRGVNRSLHGIWPGKICKGVPTHLATDVELKEIQGMMDASE
GTNYTCCKLQRFTHEWNKHGWCNWHNIDPWIQLMNRTQADLAEGPPVKECAVTCRYDKDADI
NVVTQARNRPFTTTLTGCKKGKNFSFAGTVIESPWFGAYA (SEQ ID NO:23)

Flc23
ENITQWFGAYA (SEQ ID NO:24)

Fig. 6 pPRKflc23 with an incorporated HA epitope

NON-SPREADING PESTIVIRUS

CROSS-REFERENCE TO RELATED APPLICATIONS

This application is a continuation of co-pending International Patent Application No. PCT/NL00/00153 filed on Mar. 8, 2000 designating the United States of America (International Publication No. WO 00/53766 published on Sep. 14, 2000), the contents of the entirety of which are incorporated by this reference.

TECHNICAL FIELD

The invention relates to vaccines used in the eradication or control of pestivirus infections, particularly those used in pigs or ruminants.

BACKGROUND

The genus *Pestivirus* of the family Flaviviridae conventionally consists of classical swine fever virus ("CSFV"), Border disease virus ("BDV"), and bovine viral diarrhea virus ("BVDV"). Genomes of several BVDV, BDV and CSFV strains have been sequenced, individual pestiviral proteins have been expressed and viruses derived from (full-length) DNA copies of the RNA genome of BVDV and CSFV have been generated (Renard et al., 1987, EP application 0208672; Collett et al., 1988, *Virology* 165, 191–199; Mendez et al., *J. Virol.* 72:4737–4745, 1988; Deng and Brock, 1992, *Virology* 1991, 865–679; Meyers et al., 1989, *Virology* 171, 555–567; Moormann et al., 1990, *Virology* 177, 184–188; Meyers et al., 1989, EP 89104921; Moormann and Wensvoort, 1989, PCT/NL90/00092; Moormann and Van Rijn; 1994, PCT/NL95/00214; Ridpath et al., 1997, *Virus Res.* 50: 237–243; Becker et al., 1998, *J. Virol.* 72:5165–5173, Meyers et al.,*J. Virol.* 70:1588–1595, 1996).

The pestivirus genome is a positive-stranded RNA molecule of about 12.5 kilobases containing one large open reading frame ("ORF"). The ORF is translated into a hypothetical polyprotein of approximately 4,000 amino acids, which is processed by virus- and cell-encoded proteases. The ORF is flanked by two conserved nontranslated regions, which are probably involved in the replication of the genome. The 5'-noncoding region also plays a role in initiation of translation.

The polyprotein which is co- and post-translationally processed by cellular and viral proteases contains all the viral structural and nonstructural proteins (for review, see, C. M. Rice: In Fields Virology, Third Edition, 1996 Flaviviridae: The Viruses and their Replication: Chapter 30: pp. 931–959). The viral structural proteins, the capsid protein C and the envelope proteins $E^{rns}$, E1 and E2, are located in the N-terminal part of the polyprotein. The nonstructural proteins, including the serine protease NS3 and RNA replicase complex NS5A and NS5B, are located in the C-terminal part of the polyprotein.

Pestiviruses are structurally and antigenically closely related. To date, pestiviruses such as BDV, BVDV and CSFV have been isolated from different species, most notably from ruminants and pigs, but infection of humans has also been reported. All pestiviruses have in common the ability to induce congenital infections of fetuses when a pregnant animal is infected. Such fetal infections occur via transplacental infection if the dam undergoes an acute infection during pregnancy or is persistently infected with a pestivirus (Oirschot, J. T. van, Vet. Microbiol. 4:117–132, 1979; Baker J. C., JAVMA 190:1449–1458, 1987; Nettleton P. F. et al., Comp. Immun. Microbiol. Infect. Dis. 15:179–188, 1992; Wensvoort G. and Terpstra C., Res. Vet. Sci. 45:143–148, 1988).

Currently, modified-live, killed and subunit pestivirus vaccines are available. Live-virus vaccines have the advantage over the other types of vaccines of achieving higher levels of immunity without the need of booster vaccination. However, disadvantages include the ability of vaccinal strains to cross the placenta and induce all known consequences of fetal pestivirus infection (Liess B. et al., Zentralblad Veterinarmed. [B] 31:669–681, 1984). Furthermore, modified-live pestivirus vaccines have been reported to cause immunosuppressive effects, probably due to their ability to spread through the vaccinated animal and replicate for several days in lymphocytes and neutrophils, thereby causing leukopenia and horizontal spread (Roth J. A. and Kaeberle M. L., Am. J. Vet. Res. 44:2366–2372, 1983). Furthermore, epizootics of mucosal disease (a consequence of a persistent BVDV infection) and of acute BVDV infections have been reported after vaccination with live-virus vaccines (Lambert G., JAVMA 163:874–876, 1973).

Thus, despite the fact that live vaccines are generally considered as having the best immunological properties, there are distinct downsides to using a live pestiviral vaccine in the control and eradication of pestivirus infections.

These downsides are related to the fact that a conventional live pestiviral vaccine, after inoculation of the animal with the vaccine, undergoes several rounds of replication and spreads through the vaccinated animal. For one thing, this may result in the above-reported shedding of the virus (horizontal spread), which, after all, is a normal result of any viral infection, whereby an animal is infected with a virus after which the virus replicates, spreads through the body, may replicate again, and eventually is shed from the infected animal to spread to and infect a second, contact, animal.

Even more serious, however, are congenital infections with pestiviruses, causing the so-called vertical spread. Fetuses get infected when the virus spreads through the body of a pregnant animal and the virus crosses the transplacental barrier. Depending on the time of gestation and the virulence of the infecting virus, several effects can be noticed. Severe effects include the death of embryos or fetuses, malformations, mummification, stillbirth or perinatal death (Liess B., Vol. 2 Disease Monographs (E. P. J. Gibss, Editor) Academic Press, London. pp 627–650, 1982). Less virulent virus infections, or infections later in gestation, generally result in the birth of congenitally infected offspring (van Oirschot J. T. in: Classical swine fever and related viral infections, B. Liess (ed) Martinus Nijhoff Publishing Boston pp 1–25, 1988), i.e., calves, lambs, or piglets that are commonly, persistently infected for life often do not thrive well, are prone to immunosuppression and (sub)clinical disease (such as mucosal disease with BVDV (Brownlie, J. Arch. Virol. [Suppl. 3]:73–96, 1991)) and, last but not least, are a continuing source of infection for the rest of the population.

DISCLOSURE OF THE INVENTION

The invention provides nucleic acid, pestivirus-like particles and a modified-live pestivirus vaccine comprising the nucleic acid or particle(s) which is capable of eliciting a proper immune response without having the ability to spread throughout the vaccinated animal, thereby avoiding the negative consequences of viral spread. Preferably, the immune response allows for serological discrimination between vaccinated animals and wild-type pestivirus infected animals.

Viral spread or spread of viral nucleic acid in an inoculated animal could, in theory, also be prevented by inoculating an animal with a pestiviral defective interfering particle (DI) as, for example, known from Meyers et al. (J. Virol. 70:1588–1595, 1996) or Kupfermann et al. (J. Virol. 70:8175–8181, 1996) if one could obtain the DI particles free from the helper pestivirus required for their replication, which is, for all practical purposes, near impossible. Inoculating the animal with a DI preparation containing the helper virus as well would defeat all the purposes; the helper virus would spread throughout the animal, thereby subjecting it to the undesired pestivirus infection, allowing horizontal and vertical transmission. Serological discrimination is thus also not possible, since antibodies directed against the helper virus would be detected.

However, even if one succeeded in obtaining the DI particles free of the helper virus, it still would amount to nothing; the pestiviral DI particles contain no nucleic acid that allow it to elicit a proper immune response, since the DI nucleic acid essentially does not contain the nucleic acid encoding for structural proteins or immunodominant parts thereof that are responsible for the proper immune response.

In a first embodiment, the invention provides a recombinant nucleic acid derived from a pestivirus from which nucleic acid, a fragment encoding at least one pestiviral protein or substantial part thereof related to viral spread is functionally deleted, the nucleic acid allowing for RNA replication in a suitable cell and encoding at least one functional structural protein or at least one immunodominant part thereof.

"Functionally deleted" herein comprises any insertion, modification or deletion of the viral genome that results in the production (via transcription and translation of the nucleic acid in a cell, preferably a cell suitable for the transcription and translation of the nucleic acid, preferably a cell in an animal to be vaccinated) of an at least functionally inactivated viral protein or fragment thereof that in its wild-type state is involved in viral spread, or at least in transmission to, or viral infection of, cells. Because of the inactivated protein, even when incorporated into the viral particle comprising the nucleic acid, the functional deletion has disabled the particle to enter or infect a cell which normally, had that protein or functional fragment been functioning properly in the particle, would be infected by the particle. In this way, although the particle may yet still be formed, the particle is no longer infectious for other cells and can, thus, no longer contribute via the route of infection to the spread or transmission of the particle to another cell, notwithstanding the fact that a cell, once infected, may fuse and/or divide, thereby generating multiple cells comprising the particle.

The nucleic acid provided by the invention allows for RNA replication in a suitable cell and encodes at least one functional protective protein or at least one immunodominant part thereof. In a preferred embodiment of the invention, the protective protein is a structural protein, in general, and the immunodominant parts of structural envelope proteins mount the best immune response of the pestiviral proteins. However, some non-structural proteins, such as NS3, are also capable of mounting a sufficient immune response for some purposes and can, therefore, also be included. Thus, although spread-through infection has now been prevented, the fact that RNA replication is possible allows for one or more rounds of transcription and translation in the cell of immunologically dominant proteins against which a vaccinated animal mounts an immune response through which it is at least partly protected against the consequences of infection with a wild-type pestivirus. The translated protein(s) or fragment(s) thereof in themselves (is) are responsible for the immune response and may also become part of a virus-like particle, even comprising the replicate RNA, but the particle is not infectious due to the fact that one essential functional feature of the functionally deleted protein is missing.

Although in one embodiment the nucleic acid as provided by the invention may comprise DNA, as to allow for DNA vaccination, in another embodiment, the invention provides nucleic acid wherein the nucleic acid is RNA to allow for RNA vaccination. Such RNA is, for example, packaged into a virus-like particle in a complementing cell, as provided by the invention, provided with a functional protein or fragment (derived from the complementing cell) responsible for virus-cell interactions allowing the particle to enter or infect a suitable cell, or may be introduced into the animal's cells otherwise, such as via the intradermal route.

In a preferred embodiment, the invention provides a nucleic acid wherein the functional deletion is in a fragment encoding an envelope protein. Essential to infection with pestiviruses is the interaction of viral structural proteins with the surface or a receptor of the susceptible cell. It is through this interaction that the infection takes place. Especially envelope proteins E2 and/or $E^{ms}$ provide for this interaction, and functionally deleting at least one of these envelope proteins or functional fragments thereof (in particular those fragments involved in receptor or surface interaction) leads to obstruction of infectivity.

Several examples of such functional deletions in a nucleic acid-encoding protein related to viral spread are given in the detailed description of the invention. An example comprises a modification of a cysteine-encoding nucleic acid codon, whereby a conformational change is induced in a fragment of a pestiviral protein, preferably an envelope protein, in such a way that the functionally deleted protein, when incorporated in the particle, has disabled the particle to enter an otherwise accessible cell. One example is the modification of a codon resulting in a cysteine change, for example, at amino acid position 422, or, for that matter, at position 381, of the amino acid sequence of the $E^{ms}$ protein of CSFV, or at functionally corresponding locations in the $E^{ms}$ protein of CSFV or other pestiviruses, which, for example, obtained by sequence comparison, are also provided by the invention. Another example comprises deleting larger fragments of a nucleic acid encoding a pestiviral protein, for example, by deleting at least a fragment encoding approximately corresponding positions 170–268 or other functionally related fragments of the capsid proteins C of CSFV or other pestiviruses or by deleting at least a fragment encoding approximately corresponding positions 500–665 or other functionally related fragments of the E1 proteins of CSFV or other pestiviruses, or comprises deleting fragments encoding, etc. Another example comprises deleting larger fragments of a nucleic acid encoding a pestiviral protein, for example, by deleting at least a fragment encoding corresponding positions 381, 422, 381–422, 405–436, 422–436, 422–488 or 273–488 or other functionally related fragments of the $E^{ms}$ protein of CSFV or other pestiviruses, or comprises deleting fragments encoding corresponding positions 698–1008 or 689–1062 in the E2 protein of CSFV or other functionally related fragments of the E2 protein of CSFV or other pestiviruses.

In a much preferred embodiment, the invention provides a nucleic acid wherein the functional deletion comprises an immunodominant part of the protein. For example, deleting a fragment corresponding to about amino acid positions 422–436 or 422–488 of the $E^{ms}$ protein, or corresponding to about amino acid positions 693–746, 785–870, 689–870 or 800–864 of the E2 protein or any other fragment related to a discernible immune response against the protein has the additional advantage that a discernible vaccine is provided.

By deleting the serologically discernible fragment, in the end, a marker vaccine is obtained that allows for serological discrimination between vaccinated animals and animals infected with a wild-type pestivirus.

In constructing a vaccine, one has to take into account what (type of) serological test is preferred once the vaccine is employed in the field. For CSFV, it preferably should be genotype specific, which blocks using diagnostic tests based on NS3. However, selecting E2 or $E^{ms}$ as diagnostic antigens hampers developing a vaccine which uses the protective properties of these proteins. The invention surprisingly provides a pestivirus vaccine in which a protein, preferably an envelope protein comprising a specific immunodominant part, in general, thought responsible for generating protection, has been (functionally) deleted, allowing serological discrimination surprisingly without seriously hampering protective properties.

The protective properties are optimally provided by a nucleic acid according to the invention having a fragment encoding a protective protein that is a functional structural protein, more preferably a functional envelope protein or at least one immunodominant part thereof. Most preferred by the invention is a nucleic acid comprising a fragment encoding a functional deletion in one pestiviral envelope protein, for example, E2 or $E^{ms}$, respectively, and further comprising a nucleic acid encoding another protective envelope protein, or immunodominant part thereof, for example, $E^{ms}$ or E2 or part thereof, respectively.

In a further embodiment, the invention provides a nucleic acid additionally comprising a non-pestivirus nucleic acid fragment, thereby providing a nucleic acid encoding heterologous protein or fragments thereof. Heterologous protein (fragments) may be used as a marker or may be used to elicit a (protective) immune response. Marker sequences are preferably highly antigenic and, in one embodiment of the invention, preferably derived from a (micro)organism not replicating in animals. They may encode known complete gene products (e.g., capsid or envelope proteins or antigenic parts of gene products (e.g., epitopes). Marker sequences may also encode artificial antigens not normally encountered in nature, or histochemical markers like *Escherichia coli* β-galactosidase, *Drosophila* alcohol dehydrogenase, human placental alkaline phosphatase, firefly luciferase and chloramphenicol acetyltransferase. Also provided is a nucleic acid wherein the non-pestivirus fragment is derived from a pathogen encoding one or more protein (fragments) inducing protective immunity against disease caused by the pathogen, such as a fragment derived from parvovirus, coronavirus, porcine respiratory and reproductive syndrome virus, herpesvirus, influenza virus, and numerous other pathogens known in the art. Also provided is a nucleic acid wherein the non-pestivirus fragment is derived from a cytokine inducing immuno-regulating or -stimulating signals when expressed. Numerous cytokines are known in the art, such as interleukines, interferons and tumour necrosis or colony-stimulating factors.

The invention further provides a nucleic acid according to the invention wherein the suitable cell comprises a nucleic acid construct encoding at least the pestiviral protein or substantial part thereof related to viral spread. Such a suitable cell, which is also provided by the invention, comprises a cell comprising a recombinant nucleic acid encoding at least one pestivirus protein or substantial part thereof related to viral spread and allows packaging the pestiviral protein or substantial part thereof in a pestivirus-like particle. Such a packaging or complementing cell, according to the invention, allows nucleic acid or replicate nucleic acid according to the invention to be part of a pestivirus-like particle, wherein a substantial part of the protein (fragments) composing the particle is derived from translation and transcription in the cell of nucleic acid according to the invention, being complemented with a protein (fragment) related to viral spread derived from the nucleic acid construct that is also expressed in the complementing cell. Such a protein (fragment) can be transiently expressed from a nucleic acid construct or can be expressed from a helper virus, but preferred is a cell according to the invention wherein the pestiviral protein or substantial part thereof related to viral spread is stably, either inducably or constitutively, expressed from, for example, a self-replicating nucleic acid or from the cellular genome integrated nucleic acid.

The invention also provides a method for obtaining a pestivirus-like particle comprising transfecting such a cell according to the invention with a nucleic acid according to the invention, further comprising allowing the nucleic acid to replicate in the cell, further comprising allowing replicated nucleic acid to be part of a particle comprising at least the pestiviral protein or part thereof derived from the cell, and further comprising harvesting the particle. Such a use of a nucleic acid according to the invention, or a cell according to the invention, in producing a pestivirus-like particle is provided by the invention. By transfecting the cell with nucleic acid according to the invention and allowing the nucleic acid to replicate, a replicated RNA of the nucleic acid is packaged in the pestivirus-like particle, the particle also comprising a functional protein or set of proteins related to viral spread, at least partly derived from the nucleic acid construct with which the complementing or packaging cell has also been provided. Likewise, the invention provides a pestivirus-like particle obtainable by a method according to the invention; for example, the invention provides a pestivirus-like particle (or a multitude of such particles) comprising nucleic acid derived from a pestivirus, from which nucleic acid, a fragment encoding at least one pestiviral protein, or substantial part thereof related to viral spread, is functionally deleted, the nucleic acid allowing for RNA replication in a suitable cell and encoding at least one functional structural protein or at least one immunodominant part of an immunodominant structural protein. The particle may be derived from one type of pestivirus but can also be a so-called hybrid particle, wherein its genome and part of its constituting protein (fragments) is (are) derived from one type pestivirus, such as BVDV or BDV, but wherein complementing protein (fragments) are derived from another type pestivirus, such as CSFV. The particle, having been produced in the packaging or complementing cell as provided, is itself infectious and, thus, capable of entering a suitable second cell, such as a non-complementing cell capable of being infected with a pestivirus type in general, or such as a susceptible cell in an animal to be vaccinated. When replicating in the second cell (which is non-complementing) a new particle is produced that, however, lacks the possibilities to infect yet another cell and is, thus, unable to spread by infection. Thus, when the particles produced in a complementing cell are used to infect an animal, such as when used in or as a vaccine, the particles will infect suitable cells in the vaccinated animal, from which, however, no new particles that spread by infection to other cells are generated, thereby demonstrating the requirements of a non-spreading (non-transmissible) vaccine.

The invention also provides a method for obtaining a non-spreading pestivirus vaccine comprising obtaining a multitude of particles by a method according to the invention and preparing a suspension of the particles in a suitable diluent. Suitable diluents are known in the art and preferably on a watery basis, such as a (buffered) salt solution or (growth) medium. The invention also provides a method for obtaining a non-spreading pestivirus vaccine comprising obtaining a multitude of particles by a method according to the invention and preparing a suspension of the particles in a method comprising combining the suspension with an adjuvant. Suitable adjuvants are water-oil emulsions, aluminum salts or other adjuvants known in the art, see, for example, Vogel F. R. and Powell M. F, A compendium of adjuvants and excipients. In: Vaccine design. (eds) Powell and Newmann, Pharmaceutical Biotechnology Series, Plenum, N.Y., 1994. The invention thus provides a non-spreading pestivirus vaccine obtainable by a method according to the invention. The invention provides such a vaccine comprising a nucleic acid according to the invention or a pestivirus-like particle according to the invention, for example, further comprising an adjuvant. Optimal efficacy of the vaccine is achieved if its nucleic acid is targeted to suitable antigen presenting cells. Replication and translation of the viral RNA in these cells will result in processing of viral antigen for optimal presentation to the immune system.

In one embodiment of the invention, the vaccine consists of pestivirus-like particles produced in a complementing packaging cell which, with or without an adjuvant, are applied to the animal via different routes such as, but not limited to, intranasal, intramuscular, intradermal or intravenous vaccination, or a combination of routes. In another embodiment of the invention, the vaccine consists of essentially naked DNA or RNA according to the invention which, with or without an adjuvant, is preferably applied to the animal via the intradermal route. However, alternative routes such as, but not limited to, the intramuscular route are suitable.

Such a vaccine is provided wherein the nucleic acid is derived from any pestivirus (vaccine) strain from which (full-length) cDNA and infectious copies thereof are, or can be, provided, such as C-strain virus or from another pestivirus such as another vaccine-type or wild-type of a classical swine fever virus, a bovine viral diarrhea virus or a Border disease virus, or chimeric virus. For simplicity's sake, the numbering of the C-strain sequence is used herein for all pestivirus sequences. In fact, in other pestivirus sequences, the numbering of the $E^{rns}$ and the E2 proteins in the (poly)protein may differ slightly due to length differences in the (poly)protein sequences of pestivirus strains. Based on homology, the N and C termini of the E2 or $E^{rns}$ sequence of any pestivirus strain can, however, easily be determined, such as shown by Rumenapf T. et al., J. Virol, 67:3288–3294, 1993, or Elbers K. et al., J. Virol. 70:4131–4135, 1996.

The invention also provides a method for controlling and/or eradicating a pestivirus infection comprising vaccinating at least one animal with a vaccine according to the invention. The vaccination serves to prevent or mitigate a wild-type pestivirus infection which the animal may have been or may be confronted with due to the presence of wild-type virus in its surroundings. Since no spread or shedding of the vaccine occurs, the vaccinated animal can be safely vaccinated, even when pregnant; no risk of congenital vaccinal infections of its fetus, or shedding of the vaccine from the vaccinated to a non-vaccinated animal, is present due to the non-spreading nature of the vaccine.

Additionally, the invention provides a method for controlling and/or eradicating a pestivirus infection comprising testing an animal vaccinated with a vaccine according to the invention for the presence of antibodies specific for a wild-type pestivirus. In a preferred embodiment, the method for controlling such a vaccine is used as a marker vaccine. The use of such a marker vaccine as provided by the invention allows serological discrimination between vaccinated and field-virus infected animals, and thereby a controlled elimination of the virus. For serological discrimination of pestivirus genotypes, it does not suffice to provide protection with a vaccine comprising the protective proteins E2 or $E^{rns}$ but not the NS3 protein and detecting infections with tests based on NS3. NS3 is not genotype-specific; at least it does not elicit genotype-specific antibodies to allow discrimination between genotypes. Although no objection can be seen at using the tests to diagnose BVDV or BDV infections, such diagnostic tests can, thus, hardly be used in the aftermath of vaccination campaigns against, for example, CSFV in pigs. Circulating NS3-BDV or NS3-BVDV antibodies will cause a plethora of false-positive results, leading to suspicions of CSFV infections when, in fact, there aren't any in the pig population tested. Preferably, tests are used to detect antibodies against E2, or serologically discernible fragments thereof, when the functional deletion is in the nucleic acid fragment encoding the E2 protein and the protective protein mainly comprises $E^{rns}$ protective protein or fragments thereof, optionally supplemented with other protective protein (fragments), or vice versa; tests are used to detect antibodies against $E^{rns}$, or serologically discernible fragments thereof, when the functional deletion is in the nucleic acid fragment encoding the $E^{rns}$ protein and the protective protein mainly comprises E2 protein or fragments thereof, optionally supplemented with other protective protein (fragments).

The invention also provides an animal vaccinated with a non-spreading (non-transmissible) pestivirus vaccine according to the invention. Since such an animal bears no risk of spreading the vaccine to contact animals, or to its fetus(es), such an animal has considerable advantages over animals vaccinated with conventional pestivirus vaccines. It can, for example, be traded during that period shortly after vaccination where trade otherwise has to be restricted due to the risk of shedding.

The invention is further explained in detail below without limiting the invention.

BRIEF DESCRIPTION OF THE DRAWINGS

FIG. 1 Schematic representation of $E^{rns}$ of CSFV strain C (top) and overview of $E^{rns}$ plasmids (bottom). Domains of RNase activity are shown by closed bars. Positions of cysteines are indicated with black dots.

Figure 2A:
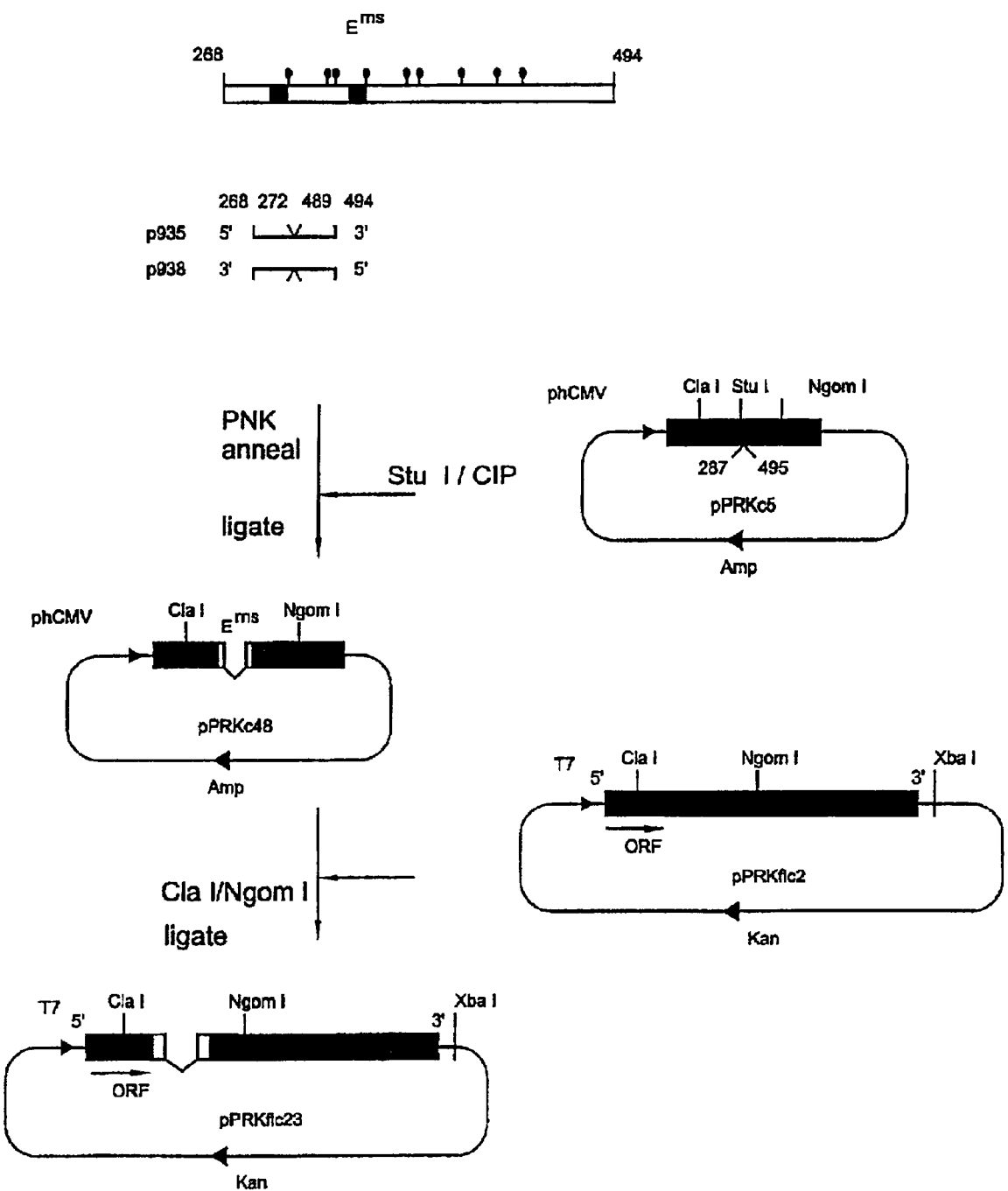

[a] Positions of the deletions or point mutations with respect to the amino acid sequence of the open reading frame (ORF) of CSFV strain C (Moormann et al., J. Virol. 1996, 70: 763–770).

[b] Cysteine-to-serine mutations are depicted with white dots.

[c] The recombinant $E^{rns}$ in these plasmids do not harbor a C-terminal HA tag.

NA: not available.

FIG. 2 Schematic representation of the construction of the full-length DNA copies pPRKflc23 (A) and pPRKflc22 (B) harbouring $E^{rns}$ deletions: The amino acid sequence numbering is of the open reading frame (ORF) of the CSFV strain C (Moormann et al., 1996, J. Virol., 70: 763–770). PCR primers are indicated with solid lines and designated: p(number); N$^{pro}$, autoprotease; C, core protein; E$^{ms}$, E1 and E2 envelope proteins; 5', 5' non-coding region; 3', 3' non-coding region, Amp, ampicillin resistance gene; CIP, calf intestinal phosphatase; Kan, kanamycin resistance gene; ORF: open reading frame; PNK, polynucleotide kinase; PhCMV, promoter-enhancer sequence of the immediate early gene of human cytomegalovirus; T7, bacteriophage T7 promotor. pPRKflc2 is the wild-type full-length cDNA copy of the CSFV strain C. (B) Plasmid pPRKc129 was the template for the first PCR of E$^{ms}$. The Nar I site of this PCR product and the Cla I site of the hemagglutinin (HA) epitope have compatible ends. These two PCR fragments were inserted into the Bgl II/Sal I digested vector pPRKc16 via a three-point ligation. See text for detailed information on the construction of the full-length DNA copies and the primer sequences.

FIG. 3 Characterization of recombinant viruses.

[a] Positions of cysteines are indicated with black dots, cysteine-to-serine mutations are depicted with white dots.

[b] Positions of the deletions or mutations with respect to the amino acid sequence of CSFV strain C (Moormann et al., J. Virol. 1996, 70: 763–770).

[c] Supernatants from SK6c26-infected cells were used for infection of SK6 and SK6c26 cells. The cells were immunostained with E$^{ms}$-specific antibodies (R716 and C5) or an E2-specific Mab (b3) and were scored as positive (+) or negative (−).

[d] Viruses are considered to be infectious viruses if supernatant of the infected cells can infect SK6 or SK6c26 cells. Spread of virus via cell-to-cell spread and spread of virus due to division of cells is not considered as infectious virus.

Figure 4:
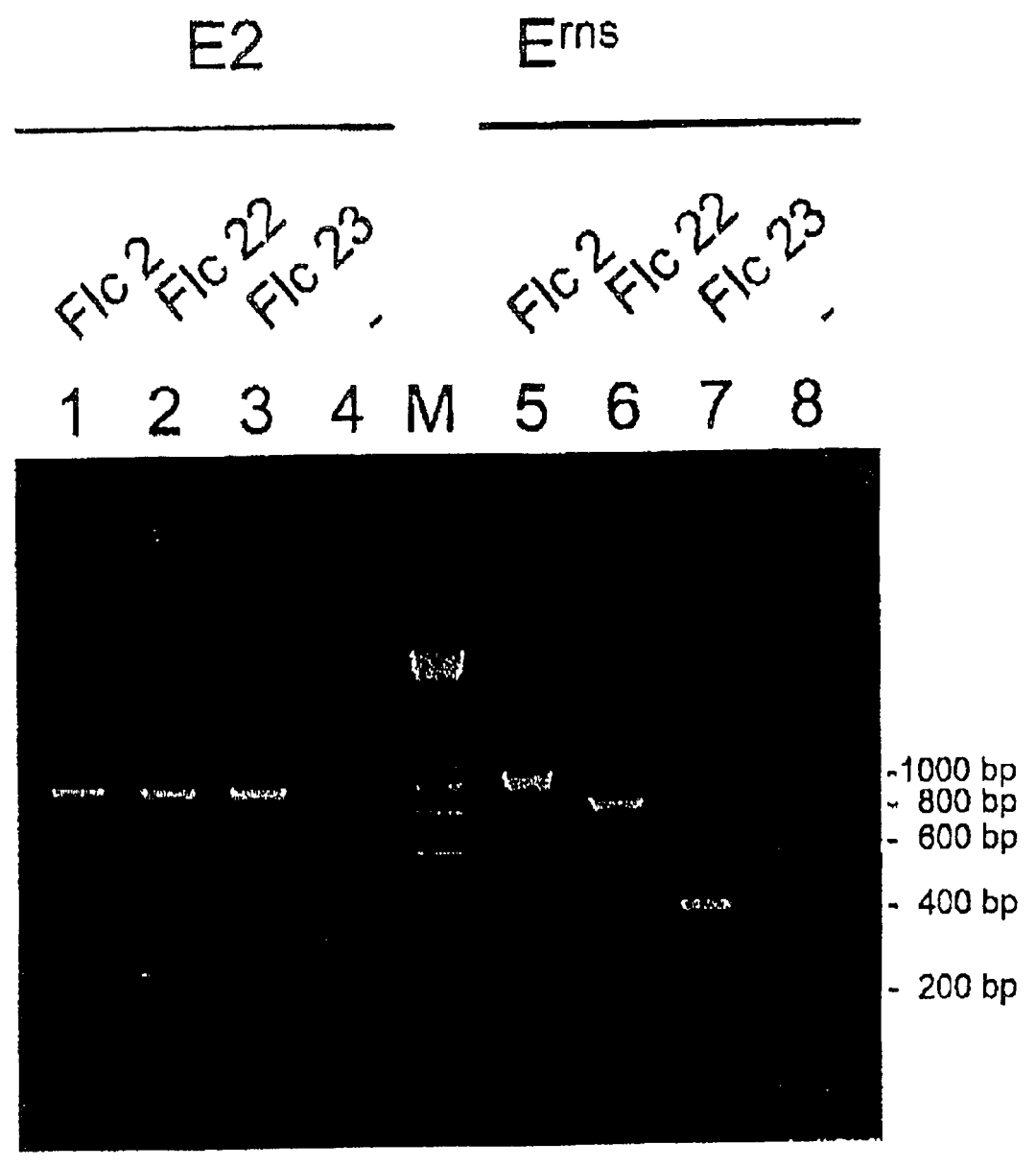

FIG. 4 RT-PCR of SK6c26 cells infected with Flc22, Flc23 and Flc2 with primers flanking E$^{ms}$ and E2. (−) negative control: mock infected SK6c26 cells; M: 200 bp marker.

FIG. 5 Growth kinetics of the recombinant CSFV viruses Flc22, Flc23 and the wild-type virus Flc2. Subconfluent monolayers of SK6c26 cells were infected at a multiplicity of 0.1. Viruses were adsorbed for 1.5 hr. Virus titers of the cell lysates and supernatant at various time points were determined by end point dilution on SK6c26 cells.

FIG. 6 E$^{ms}$ amino acid sequence of the recombinant Flc22, Flc23 and the wild-type strain Flc2, |: indicates position of deletion.

Figure 7:
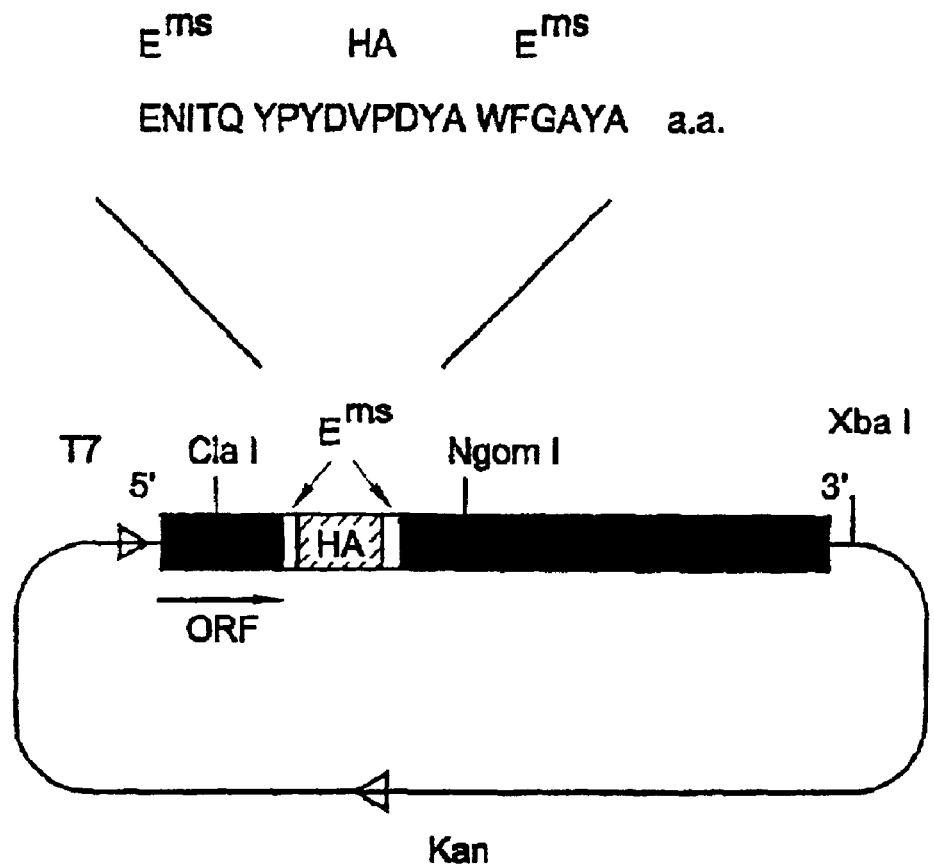

FIG. 7 Schematic representation of pPRKflc23 harbouring the HA epitope, a non-pestivirus sequence. The HA epitope is flanked by the 5 utmost N-terminal amino acids and 6 utmost C-terminal amino acids of E$^{ms}$.

FIG. 8 Schematic representation of the construction of the full-length DNA copies pPRKflc4 (A) and pPRKflc47 (B). The amino acid sequence numbering is of the open reading frame (ORF) of the CSFV strain C (Moormann et al., 1996, J. Virol.). PCR primers are indicated with solid lines and designated: p(number); N$^{pro}$, autoprotease; C, core protein; E$^{ms}$, E1 and E2 envelope proteins; p7: p7 protein, NS, nonstructural protein, 5', 5' non-coding region; 3', 3' non-coding region, Amp, ampicillin resistance; Kan, kanamycin resistance. pPRKflc2 is the wild-type full-length DNA copy of the CSFV strain C. (A) The E2 gene of plasmid pPAB16 was inserted in plasmid pPRKc129 by NgoMI/BglII digestion. (B) pPRKflc2 was the template for PCR amplification with primers p1195 and p403. See text for detailed information on the construction of the full-length DNA copies and the primer sequences.

EXAMPLES

Example 1

Construction and Characterization of Recombinant CSFV Strains Flc22, Flc23, Flc30, Flc31, Flc32, and Flc33

Materials and Methods

Cells & Viruses

Swine kidney cells (SK6-M, EP 0 351 901 B1) were grown in Eagle's basal medium containing 5% fetal bovine serum, glutamine (0.3 mg/ml), and the antibiotics penicillin (200 U/ml), streptomycin (0.2 mg/ml), and mycostatin (100 U/ml). Fetal bovine serum was tested for the absence of BVDV and BDV antibodies as described previously (Moormann et al., 1990, Virology 177:184–198).

Recombinant CSFV strain C viruses Flc22, Flc23, Flc30, Flc31, Flc32, and Flc33 were grown and prepared as described earlier (Moormann et al., 1996, J. Virol. 70: 763–770) with a slight modification, the growth medium of SK6 cells was changed in supplemented Eagle's basal medium. Virus stocks were prepared by passaging the virus eight to ten times on SK6c26 cells. The obtained virus titres ranged from 5.0 to 5.8 TCID50/ml.

Construction of a Stable SK6 Cell Line Expressing E$^{ms}$

Plasmid pPRKc16 contains the E2 gene of CSFV strain C under control of the transcription and translation signals of expression vector pEVhisD12. Plasmid pEVhisD12 is a vector that contains promoter/enhancer sequences of the immediate early gene of the human cytomegalovirus followed by a translation initiation codon and the histidinol dehydrogenase gene (hisD) under control of the SV40 early promoter, which can be used as a selective marker (Peeters et al., 1992, J. Virol. 66: 894–905). The E$^{ms}$ gene of the CSFV strain C was amplified by PCR reaction with primers p974 5' AAG AAA AGA TCT AAA GCC CTA TTG GCA TGG 3' (SEQ ID NO:1) and p976 5' TT GTT ACA GCT GCA TAT GTA CCC TAT TIT GCT TG 3' (SEQ IC NO:2). After BglII digestion, the PCR fragment was ligated into the vector pPRKc16, which was digested with SalI, filled in, and subsequently digested with BglII. The resulting plasmid pPRKc26 contains the E$^{ms}$ gene of the CSFV strain C.

For transfection of SK6 cells with pPRKc26, lipofectamine (20 μg) (Gibco-BRL) was diluted in 50 μl of Optimem-I (Gibco-BRL) mixed with plasmid DNA (1 μg) diluted in 50 μl Optimem-I (Gibco-BRL) and this mixture was allowed to settle for 15 min at room temperature. SK6 cells grown in 10 cm$^2$ tissue culture plates were washed with Optimem-I. Fresh Optimem-I was added (0.5 ml), followed by the DNA transfection mixture. After 4 h of incubation at 37° C., the transfection mixture was removed and the wells were supplied with medium containing 5 mM histidinol. After 24 h of incubation at 37° C., cells were trypsinized and plated on a 90 mm2 plate. Medium was replaced every 34 days. After 15 days, single colonies were picked and plated into 2 cm$^2$ plates. Expression of E$^{ms}$ was determined by immunostaining of the cells with Mabs C5 (Wensvoort 1989, Thesis, University of Utrecht) directed against E$^{ms}$ of CSFV strain C. A second round of cloning was performed by trypsinizing and plating the cells in ten-fold dilution in microtiter plates in medium containing 5 mM histidinol. Wells with individual colonies were trypsinized and expression of E$^{ms}$ was determined by immunostaining (Wensvoort et al., 1988, Vet. Microbiol. 17, 129–140) the cells with Mab C5. The established SK6 cell line constitutively expressing E$^{ms}$ was named SK6c26.

Characterization of the Stable Cell Line SK6c26

E$^{ms}$ expression of the cell line SK6c26 line was tested in an immunoperoxidase staining with E$^{ms}$-specific monoclonal antibodies (Mabs) C5, specific for $E^{ms}$ of strain C (Wensvoort 1989, Thesis, University of Utrecht), 140.1 and 137.5 directed against $E^{ms}$ of CSFV strains C and Brescia (de Smit et al., unpublished data), and a polyclonal rabbit serum, R716 (Hulst et al., J. Virol. 1998, 72: 151–157). The RNase activity of the $E^{ms}$ expressed in the SK6c26 cell line was measured by a modification of the method of Brown and Ho (Plant Physiol. 1986, 82: 801–806) as described by Hulst et al., (J. Virol. 1998, 72: 151–157). The amount of $E^{ms}$ was determined by an indirect ELISA based on Mab C5 as coating antibody and horseradish peroxidase conjugated Mab 140.1 as detection antibody as described by Hulst et al. (J. Virol. 1998, 72: 151–157).

Construction of Recombinant CSFV $E^{ms}$ pPRKc5 (Hulst et al., Virol. 1998, 72: 151–157) is a pEVhisD12 derivative which contains the nucleotide sequence of the autoprotease and structural genes of CSFV strain C, without $E^{ms}$ (Npro-C and E1-E2, amino acids (a.a.) 5–267 and 495–1063 of the amino acid sequence of CSFV strain C) (Moormann et al., 1996, J. Virol. 70: 763–770). A unique Stu I site was introduced in pPRKc5 at the position where $E^{ms}$ was deleted.

Figure 1:
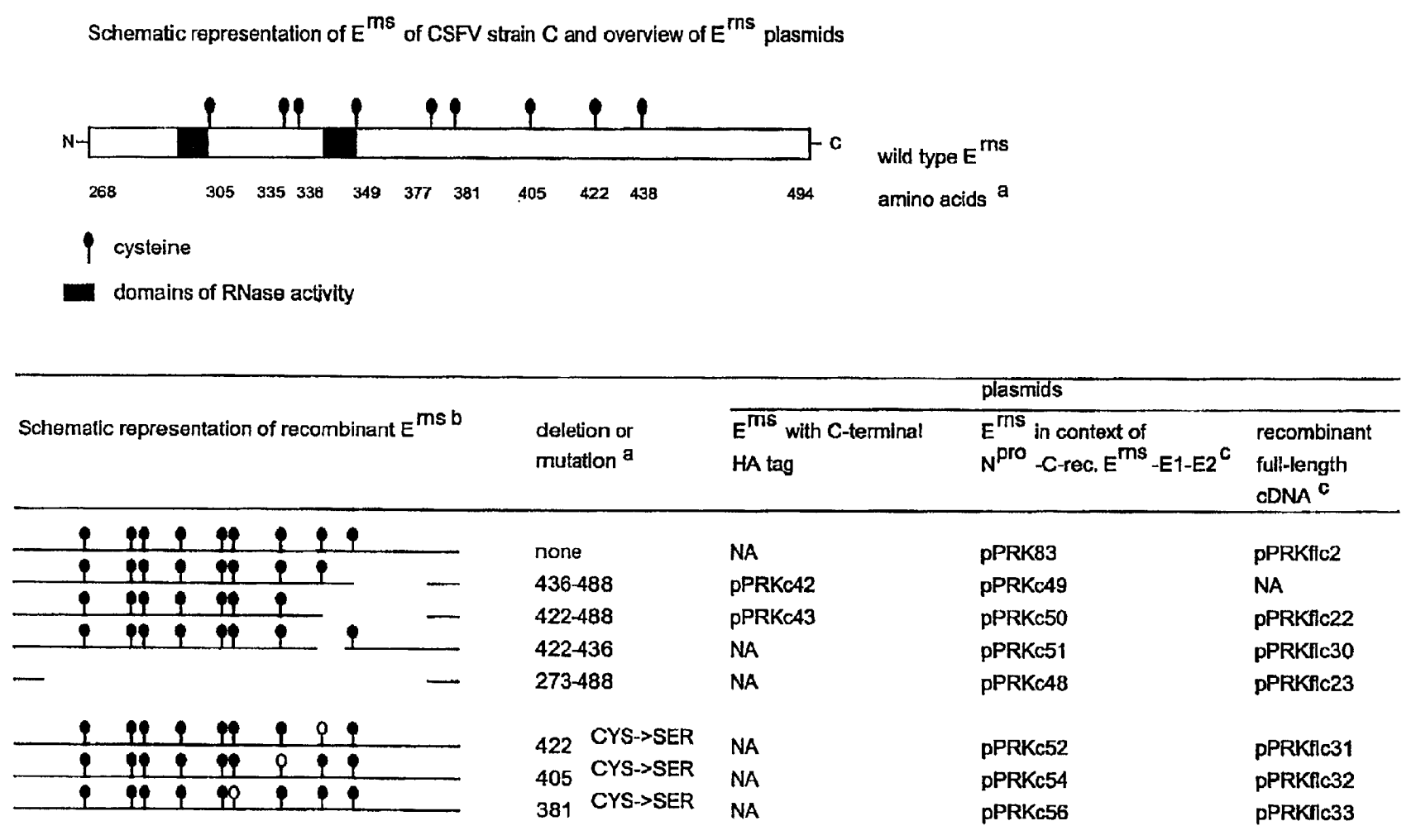

Two complementary oligomers, the forward oligomer p1135 (5'CCG AAA ATA TAA CTC AAT GGT TTG GCG CTT ATG 3'(SEQ ID NO:3)) and the reverse oligomer p1136 (5'CAT AAG CGC CAA ACC ATT GAG TTA TAT TTT CGG 3' (SEQ ID NO:4)) were phosphorylated with T4 DNA kinase, hybridized and inserted via ligation in an alkaline phosphatase-treated StuI-digested vector pPRKc5. This construct was named pPRKc48. This construct harbors the five utmost N-terminal amino acids and the six utmost C-terminal amino acids of $E^{ms}$ (deletion a.a 273–488) (FIG. 1 and FIG. 2A).

Figure 2B:
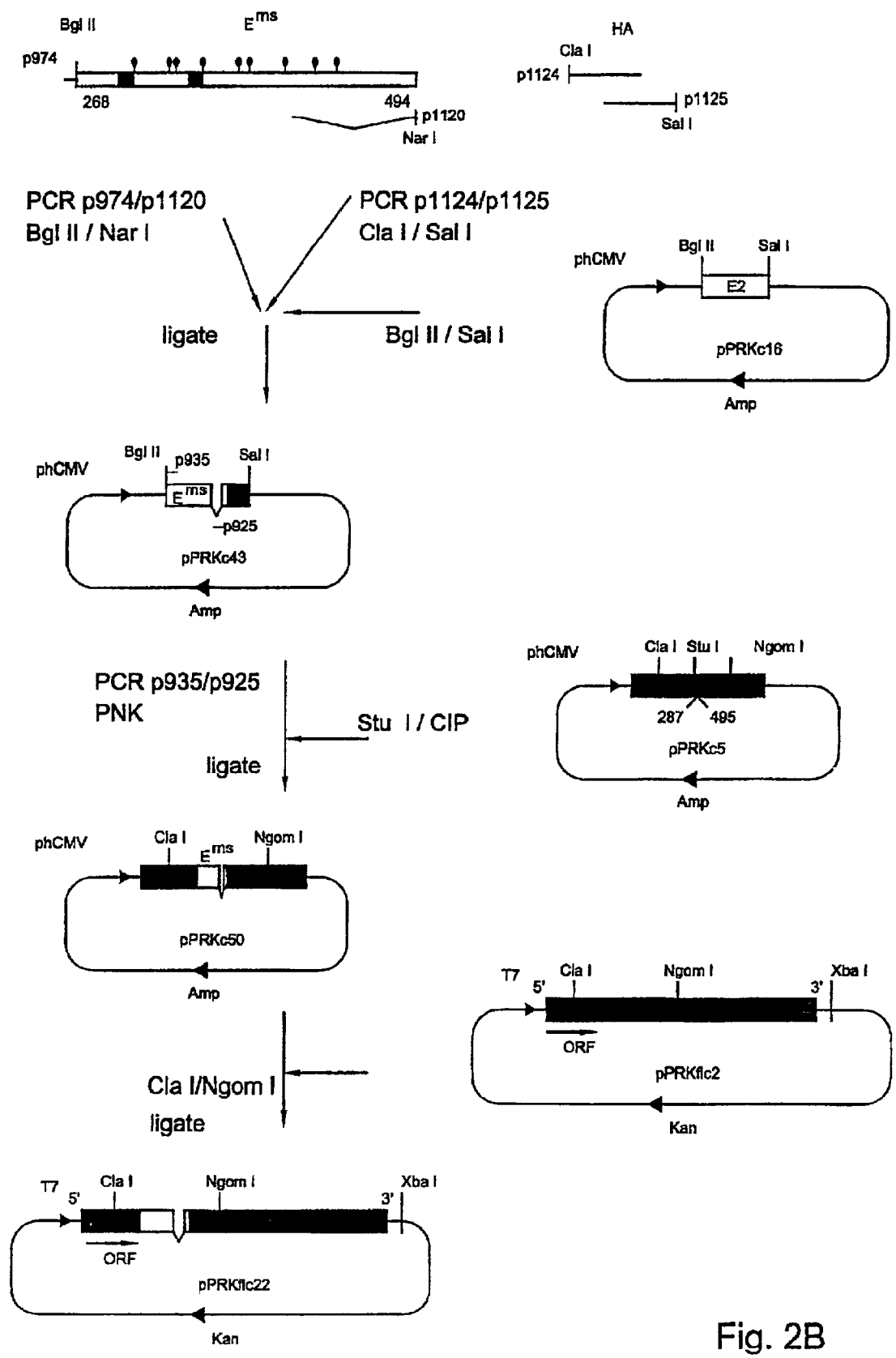

A deletion of amino acids 422 to 488 in $E^{ms}$ of strain C was accomplished by PCR amplification of the $E^{ms}$ gene using the forward primer p974 and reverse primer p1120 5' GAC GGA TTC GGC ATA GGC GCC AAA CCA TGG GCT CTC TAT AAC TGT AAC 3' (SEQ ID NO:5). The HA epitope, amino acid sequence YPYDVPDYA (SEQ ID NO:6) (Wilson et al., Cell 1984, 37, 767–778), was constructed by annealing the 3' complementary nucleotides of p1124 '5 GAC AGA TCT ATC GAT TAC CCA TAC GAT GTT CCA GAT 3' (SEQ ID NO:7) and p1255 5'GAC GTC GAC GGA TCC AGC GTA ATC TGG AAC ATC 3' (SEQ ID NO:8) (underlined is the HA sequence) and filling in the 5' single strand nucleotides in a PCR with Vent polymerase (New England Biolabs). The HA epitope PCR product was digested with ClaI/SalI, and the $E^{ms}$ PCR product was digested with BglII/NarI. The two digested PCR products were ligated via a three-point ligation into the vector pPRKc16 which was digested with BglII and SalI. This resulted in plasmid pPRKc43 containing a recombinant $E^{ms}$ with a deletion of amino acids 422 to 488 with C terminally an HA epitope (FIG. 1 and FIG. 2B). After PCR amplification of plasmid pPRKc43 with the forward primer p935 (5'CCG AAA ATA TAA CTC AAT GG 3' (SEQ ID NO:9)) and the reverse primer p925 (5'CAT AAG CGC CAA ACC AGG TT 3' (SEQ ID NO:10)), the PCR product was phosphorylated with T4 DNA kinase and subsequently ligated into the alkaline phosphatase treated StuI digested vector pPRKc5. The resulting construct harbouring the nucleotide sequence of the autoprotease, the structural proteins of strain C and the recombinant $E^{ms}$ lacking amino acids 422 to 488 was named pPRKc50 (FIG. 2B).

A deletion mutant lacking amino acids 436 to 488 of $E^{ms}$ of strain C was accomplished by PCR amplification of the $E^{ms}$ gene using the forward primer p974 and reverse primer p1121 (5' GAC GGA TTC GGC ATA GGC GCC AAA CCA ATC CCC ATA CAA GGT ATC CTC 3' (SEQ ID NO:11)). After BglII/NarI digestion, the fragment was ligated with the ClaI/SalI digested HA epitope PCR product via a three-point ligation in the vector pPRKc16, which was digested with BglII/SalI. The resulting plasmid, pPRKc42, was PCR amplified with the forward primer p935 and reverse primer p925. This PCR product was phosphorylated with T4 DNA kinase and subsequently ligated into the alkaline phosphatase-treated StuI-digested vector pPRKc5. The resulting construct harbouring the nucleotide sequence of the autoprotease, the structural proteins of strain C and the recombinant $E^{ms}$ lacking amino acids 436–488 is named pPRKc49.

A deletion mutant lacking amino acids 422 to 436 was made by PCR amplification of plasmid pPRKc129 with the primers p1147 (5' CAA ACT GCC GCA CTC ATG TGG GCT CTC TAT AAC TGT 3' (SEQ ID NO:12)) and p925. Then, the obtained PCR product was isolated from agarose gel and used as reverse primer in a second PCR reaction with primer p935 as forward primer for amplification of pPRKc129. This second PCR product was kinated and ligated into the alkaline phosphatase-treated StuI-treated vector pPRKc5, resulting in plasmid pPRKc51.

A cysteine (CYS) to serine (SER) substitution at amino acid position 422 was constructed by PCR amplification of pPRKc129 with the forward primer p1140 5' GAG AGC CCT TCG AAT TTC AAT GT 3' (SEQ ID NO:13)) and the reverse primer p925. Further steps were equal to those of the deletion mutant lacking amino acids 422 to 436. Plasmid pPRKc52 contains the autoprotease gene and the structural proteins of strain C, with a mutated $E^{ms}$ containing a CYS-to-SER substitution at pos 422.

A cysteine to serine mutation at amino acid position 405 was constructed by PCR amplification of pPRKc129 with the forward primer p1148 (5'CCT GAC CGG TTC GAA GAA AGG GAA-3' (SEQ ID NO:14)) and the reverse primer p925. Further steps were equal to those of the deletion mutant lacking amino acids 422 to 436. Plasmid pPRKc54 contains the autoprotease gene and the structural proteins of strain C, with a mutated $E^{ms}$ containing a CYS-to-SER mutation at pos 405.

A cysteine to serine substitution at amino acid position 381 was constructed by PCR amplification of pPRKc129 with the forward primer p1149 (5' TGC GCT GTG ACT AGT AGG TAC GAT AAA-3' (SEQ ID NO:15)) and the reverse primer p925. Further steps were equal to those of the deletion mutant lacking amino acids 422 to 436. Plasmid pPRKc56 contains the autoprotease gene and the structural proteins of strain C, with a mutated $E^{ms}$ containing a CYS-to-SER mutation at position 381.

Clones in which the mutated $E^{ms}$ gene were inserted in the right orientation were transfected into SK6 cells and tested for expression of $E^{ms}$ and E2 by immunostaining with antibodies against $E^{ms}$ (C5, 140.1, 137.5, R716) and E2 specific Mabs b3 and b4 (Wensvoort 1989, J. Gen. Virol. 70:2865–2876).

Construction of Full-Length CSFV Constructs Harbouring $E^{ms}$ Deletion Mutants A ClaI/NgoMI fragment of pPRKc48 and pPRKc50 was isolated and ligated into the ClaI/NgoMI digested vector pPRKflc2, formerly named pPRKflc133 (Moormann et al., 1996, J. Virol. 70: 763–770) and the resulting full-length cDNA CSFV strain C $E^{ms}$ mutants were named pPRKflc23 and pPRKflc22. The complete construction scheme of the full-length constructs pPRKflc22 and pPRKflc23 is depicted in FIGS. 2A and 2B and an overview of the $E^{ms}$ plasmids is given in FIG. 1.

Similarly, the 422–436 deletion mutant of pPRKc51 and the CYS-to-SER substitutions of pPRKc52, pPRKc54, pPRKc56, were transferred to the vector pPRKflc2 via a ClaI/NgoMI digestion, resulting in the recombinant full-length cDNA clones pPRKflc30, pPRKflc31, pPRKflc32, and pPRKflc33, respectively.

Isolation of Recombinant Viruses

Plasmid DNA from pPRKflc22, pPRKflc23, pPRKflc30, pPRKflc31 pPRKflc32, and pPRKflc33 was purified on columns (Qiagen) and linearized with XbaI. The DNA was extracted with phenol-chloroform, precipitated with ethanol, and dissolved in water. RNA was transcribed from the linearized plasmid (1 $\mu$g) in a 100 $\mu$l reaction volume containing 40 mM Tris HCl (pH 7.5), 6 mM MgCl2, 2 mM spermidine, 10 mM dithiothreitol, 40 U rRNAsin (Promega), 0.5 mM each rNTP, and 35 U T7 RNA polymerase (Pharmacia). After 1 h incubation at 37° C., 10 U RNase-free DNaseI (Pharmacia) was added and the mixture was incubated for another 15 min. RNA was extracted with phenol-chloroform, precipitated with ethanol, and dissolved in 10 $\mu$l water.

For RNA transfection, 10 $\mu$g Lipofectin was diluted in 50 $\mu$l of Optimem-I. After a 45 min incubation at room temperature, 1 $\mu$g RNA diluted in 50 $\mu$l Optimem-I was added and incubated for an additional 15 min. SK6c26 cells grown in 10 cm$^2$ tissue culture plates were washed with Optimem-I and incubated with the RNA transfection mixture for 4 h at 37° C. Then, the wells were supplied with fresh medium and incubated for 4 days at 37° C. RNA transfection was performed in duplicate. One sample was immunostained with Mabs b3/b4 specific for E2. When the E2 immunostaining proved to be negative, the duplicate sample was passaged and split into two samples. One of these samples was used for immunostaining four days after passaging. From wells in which E2 expression was observed, supernatant was applied onto fresh SK6c26 or SK6 cells to determine the presence of infectious virus. After four days, the monolayers were fixed and immunostained as described above.

Growth Kinetics of Flc22 and Flc23

Growth kinetics of the viruses was determined in SK6c26 cells. Subconfluent monolayers in M24 wells were infected at a multiplicity of infection of 0.1. Viruses were adsorbed for 1.5 h. Before cells were supplied with fresh medium, the first sample at time point zero was collected. At 0, 1, 2, 3, 4, 5, 6, and 7 days after infection the M24 plates were freeze/thawed twice and clarified by centrifugation for 10 min at 5000×g at 4° C. Virus titres (log TCID50 per milliliter) of total lysates (cell lysates plus supernatant) were determined on SK6c26 cells.

Characterization of Recombinant E$^{ms}$ Viruses

The E$^{ms}$ genes of Flc22 and Flc23 were sequenced. Therefore, cytoplasmic RNA of SK6c26 cells infected with these respective viruses was isolated using the RNeasy total RNA isolation kit (Qiagen). DNA fragments covering the E$^{ms}$ genes were analyzed by RT-PCR using primers p1154 (5' GTT ACC AGT TGT TCT GAT GAT 3' (SEQ ID NO:16)) and p305 (5' GGG GTG CAG TTG TTG TAT CCA 3' (SEQ ID NO:17)) amplifying nucleotide sequences 865 to 1920, analyzed on a 1.5% agarose gel in 1×TAE, and purified on Costar Spin-X columns. An RT-PCR of the E2 gene was performed with primer pair p307 (TGG AAT GTT GGC AAA TAT GT (SEQ ID NO:18)) and p304 (CAC TTA CCT AT[A,G] GGG TAG TGT GG (SEQ ID NO:19)) amplifying nucleotide positions 2200–3174.

Sequences of the purified PCR fragments were determined by PCR cycle sequencing using the Big dye dRhodamine terminator ready reaction cycle sequencing kit (PE) according to the manufacturer's conditions with flanking primers and analyzed on a 310 ABI PRISM genetic analyzer.

In addition, the recombinant viruses were characterized by an immunoperoxidase monolayer assay. For this, SK6 cells were infected with the recombinant viruses and Flc2. After incubation for 4 days at 37° C., monolayers were immunostained with Mabs specific for CSFV E2 (Mabs b3/b4), CSFV E$^{ms}$ Mabs 140.1, C5, 137.5 and a polyclonal rabbit serum against E$^{ms}$ R716.

Virus neutralization index (log reduction of virus titre [TCID50/ml] by neutralizing serum) was determined at a 1:250 dilution of serum 716 specifically directed against E$^{ms}$ of CSFV strain C and at a 1:1000 dilution of a pig serum 539 specifically directed against E2 of CSFV strain Brescia (Hulst et al., Virol. 1998, 72: 151–157). The virus stocks of Flc2, Flc22 and Flc23 were titrated by endpoint dilution in the presence or absence of these CSFV neutralizing antibodies.

Results

Transient Expression of Recombinant E$^{ms}$ in SK6 Cells

Previous studies showed that the antibodies raised against CSFV E$^{ms}$ do not inhibit RNase activity (Hulst et al., 1998, J. Virol. 72:151–157). The active domains of the E$^{ms}$ RNase are located in the N-terminal half of the protein (Schneider et al., 1993, Science 261: 1169–1711, Hulst et al., 1994, Virol. 200: 558–565). (See FIG. 1 for a schematic representation of E$^{ms}$.) Pepscan analysis did not reveal any linear epitopes on E$^{ms}$ for the antibodies C5, 140.1 and 137.5 (data not shown), showing that the epitopes are conformational. Therefore, a set of E$^{ms}$ recombinants were constructed with deletions of different lengths in the C-terminus (FIG. 1). These deletion mutants were constructed in an expression plasmid pPRKc5 harbouring the nucleotide sequence of the autoprotease and the structural genes (Npro-capsid-E1-E2) without E$^{ms}$. Expression of these constructs enabled us to use the E2 gene as control for a correct open reading frame since the E2 gene is located C-terminally of the E$^{ms}$ gene. SK6 cells were transfected with these plasmids and an immunoperoxidase staining was performed 24 hours after transfection (Table 1).

Cells transfected with the plasmid pPRKc49, harbouring a deletion from amino acid positions 436 to 488, can be specifically immunostained with all antibodies recognizing CSFV E$^{ms}$ (Mab C5, 140.1, 137.5) and the polyclonal serum R716, like the wild-type plasmid pPRK83. Plasmid pPRKc50, however, harbouring a deletion from position 422 to 488, is not recognized anymore by the antibodies against E$^{ms}$, but is positive with Mabs b3/b4 against E2. These results show the presence of a distinct antigenic domain on E$^{ms}$ and/or an important role for amino acids 422 to 436 for either binding or conformation of the epitopes on E$^{ms}$. This region contains a cysteine on position 422 which might be involved in the conformational structure of E$^{ms}$.

To investigate the role of this region, plasmid pPRKc51 harbouring the small deletion of amino acids 422–436 was constructed. As is shown in Table 1, immunoperoxidase staining of the transfected cells showed only Mab binding to E2, and not to E$^{ms}$. These results showed the importance of this region for the conformation of these E$^{ms}$ epitopes.

Establishment of an SK6 Cell Line Expressing CSFV E$^{ms}$

SK6 cells were transfected with plasmid pPRKc26 harbouring the CSFV strain C E$^{ms}$ gene and the histidinol (hisD) resistance gene. After 3 weeks, colonies surviving 5 mM histidinol selection were screened for the expression of E$^{ms}$ by immunostaining the cells with Mab C5 specific for CSFV E$^{ms}$. Positive cells were cloned once again to ensure clonality.

One of the clones obtained showed expression of $E^{rns}$ in more than 95% of the cells and this clone was named SK6c26. This cell line produced substantially higher amounts of $E^{rns}$ than the five other clones obtained, as was determined by immunostaining. Continuous passaging of this cell line SK6c26 in the presence of 5 mM histidinol retained persistent expression in more than 95% of the cells for at least 10 months (46 passages). Passaging in the absence of histidinol for 10 passages resulted in a slight decline of $E^{rns}$-expressing cells to approximately 80%.

The stable cell line was further characterized with respect to the biochemical characteristics of produced $E^{rns}$. The SK6c26 cell line reacted in an IPMA with all tested $E^{rns}$ antibodies (Table 2A). The amount of $E^{rns}$ in the cell lysates of SK6c26 and SK6 cells infected with Flc2 was determined by an indirect ELISA and extrapolated from a standard curve prepared from an immuno-affinity purified preparation of $E^{rns}$, prepared in insect cells.

Lysates of SK6c26 cells reacted with the $E^{rns}$ specific Mab and polyclonal antibodies in an indirect ELISA like the wild-type $E^{rns}$ (Table 2B). The amount of $E^{rns}$ produced in the SK6c26 cells (10 ng per cm$^2$) was 3-fold lower than SK6 cells infected with Flc2 (30 ng per cm$^2$). The SK6c26 cells and the Flc2-infected SK6 cells possessed comparable RNase activity as measured by an antigen capture RNase assay (Table 2B). The $E^{rns}$ protein of the stable cell line had a similar mobility as the wild-type $E^{rns}$ as determined by SDS-PAGE and was efficiently dimerized like the $E^{rns}$ found in virions (Thiel et al., 1991, J. Virol. 65:4705–4712) (Table 2B).

Construction and Recovery of C Strain CSFV $E^{rns}$ Recombinant Viruses Flc22 and Flc23

Two recombinants of the $E^{rns}$ gene were replaced in pPRKflc2, the full-length infectious copy of the CSFV strain C (Moormann et al., 1996, J. Virol. 70: 763–770). Full-length clone pPRKflc22 is derived from pPRKc50 which possessed a deletion of amino acids 422 to 488 in $E^{rns}$ (FIG. 1). The full-length clone pPRKflc23 is derived from pPRKc48 and harbors the five utmost N-terminal amino acids and the six utmost C-terminal amino acids of $E^{rns}$ (deletion of amino acids 273–488) (FIG. 1). FIGS. 2A, 2B show a schematic representation of the construction of these recombinant $E^{rns}$ full-length clones.

RNA transcribed from the linearized full-length cDNA was transfected into the SK6 cell line expressing $E^{rns}$. Four days after transfection, immunoperoxidase staining of the monolayer with Mab b3 did not show E2 expression, even with RNA transcribed from pPRKflc2. The amount of E2 protein of the recombinant virus might be too low to detect by immunostaining. Therefore, the cells were passaged to obtain higher titres of viruses. One passage after transfection, wild-type virus Flc2 was obtained, while four passages after transfection, expression of E2 could be detected with the recombinant clones pPRKflc22 and pPRKflc23. Three to five additional passages were required to obtain a virus titre of approximately 5.5 TCID50/ml and this stock was used for further characterization of the viruses, which were named Flc22 and Flc23 for the clones pPRKflc22 and pPRKflc23, respectively.

Supernatants from SK6c26 cells infected with Flc22 and Flc23 were used for infection of SK6c26 and SK6 cells. Four days after infection, for both viruses, approximately 50–70% of the SK6c26 cells were positive by E2 immunoperoxidase staining, whereas infection on SK6 cells resulted in only single cells or pairs of single cells expressing E2. Taking into account that cells infected with CSFV divide normally (once in 24 h), the number of positive cells observed on SK6c26 cells indicated replication and secondary spread of the mutated virus. Since only single cells or pairs of single cells expressed E2 in the SK6 cells, this indicates that supernatants derived from the SK6c26 cells contain infectious virus which can infect and replicate in SK6 cells but that there is no cell-to-cell spread or secondary infection of the mutated viruses in these cells.

Supernatant or cell lysates of SK6 cells infected with Flc22 and Flc23 were used for infection of new SK6 and SK6c26 cells, but this also did not lead to infected cells. For the infection of pestiviruses, the interaction of the viral envelope proteins E2 and $E^{rns}$ with the cellular surface are considered to be essential. Due to the absence of $E^{rns}$ in the SK6 cells, no infectious particles could be formed from the viruses Flc22 and Flc23.

Thus, the supernatants of the infected SK6 cells did not contain infectious virus (FIG. 3), whereas supernatant of SK6c26-infected cells with Flc22 and Flc23 can infect SK6 and SK6c26 cells and, thus, contained infectious virus.

SK6 cells infected with Flc22 and Flc23 derived from the supernatants of the SK6c26 cells could be immunostained with Mabs directed against E2, but no positive cells were found with antibodies against $E^{rns}$ (Mabs C5 and R716). As control, infection of SK6 cells with supernatant of SK6c26 cells infected with Flc2 resulted in a positive immunoperoxidase staining for both E2 and $E^{rns}$ and secondary infection (FIG. 3).

Transfection of linearized full-length cDNAs pPRKflc22 and pPRKflc23 into an SK6-cell line constitutively expressing the bacteriophage T7 RNA polymerase in the cytoplasm of the cell (Van Gennip, 1999, J. Virol. Methods, accepted for publication), resulted in transient expression of E2 after transfection, but passaging the transfected cells six times did not result in the recovery of infectious recombinant viruses (data not shown).

Taken together, these results show that the recombinant $E^{rns}$ mutant viruses Flc22 and Flc23 require complementation of $E^{rns}$ by the complementing cell line for packaging of the recombinant virus genome to yield infectious virus.

Characterization of Recombinant CSFV Viruses Flc22 and Flc23

To confirm the presence of the mutations in the genomes of Flc22 and Flc23, cellular RNA from infected SK6c26 cells was analyzed with RT-PCR with CSFV-specific primers. The fragments, after RT-PCR with primers flanking the $E^{rns}$ gene, were of the expected sizes of approximately 857, 401, and 1055, respectively for Flc22, Flc23, and Flc2, whereas the RT-PCR product of the E2 gene was for all viruses of the expected size of 974 bp. (FIG. 4). The amplification products of the $E^{rns}$ gene were sequenced, and the obtained sequences were as expected. No reversion to the wild-type or recombination with the $E^{rns}$ gene encoded by the cell line was observed.

Growth kinetics of Flc22 and Flc23 and the wild-type Flc2 were determined on the complementing cell line SK6c26. As shown in FIG. 5, the multi-step growth curve of the recombinant viruses Flc22 and Flc23 were very similar, but showed a slower growth compared to the parent virus Flc2. Titres between 5.0–5.8 TCID50/ml were reached by the recombinant viruses after 6 days, whereas the parent strain Flc2 reached this titre already within 3 days. The observed titre obtained for Flc2 4 days after infection in the complementing cell line is ten-fold lower than obtained on the parental cell line SK6 (6.8 TCID50/ml).

Experiments were conducted to determine whether $E^{rns}$ was incorporated into the viral envelope. Therefore, virus stocks of Flc2, Flc22 and Flc23 were titrated in the presence of CSFV neutralizing antibodies. Table 3 shows the reduction of virus titre by incubation with neutralizing antibodies. All recombinant viruses were neutralized to the same extent as the parent virus Flc2 with both the $E^{ms}$-specific and E2-specific neutralizing polyclonal antibodies. $E^{ms}$ on the viral envelope of Flc22 could be derived from the complementing cell line as well as from the recombinant $E^{ms}$ protein encoded by the viral genome, but the recombinant $E^{ms}$ of Flc22 is not recognized by the polyclonal serum R716 (FIG. 3) used for neutralizing the viruses. Thus, the similar neutralization index obtained with this polyclonal serum shows that the amount of $E^{ms}$ derived from the complementing cell line in the viral envelopes of Flc22 was comparable with those of Flc2 and Flc23.

FIG. 6 shows the amino acid sequence of Flc22 and Flc23 in comparison with Flc2. Flc23 is an $E^{ms}$ deletion mutant in which the cleavage site between C-$E^{ms}$ as well as $E^{ms}$-E1 were left intact; the presence of these cleavage sites might influence viability of this virus.

Construction of pPRKflc30, pPRKflc31, pPRKflc32, and pPRKflc33

The results of Table 1 show an important role for the amino acid region 422–436 for the conformation of the epitopes of our $E^{ms}$ antibodies. This region contains on position 422 a cysteine, which might be responsible for epitope recognition. To study the role of this region, we constructed a set of recombinant $E^{ms}$ full-length clones: one lacking amino acids 422–436 (pPRKflc30), a cysteine-to-serine mutant on position 422 (pPRKflc31), and two additional cysteine-to-serine mutants on positions 405 and 381 (pPRKflc32 and pPRKflc33, respectively) (FIG. 1).

RNA transcribed from the linearized full-length cDNAs was transfected into the SK6c26 cell line. The cells became positive after immunostaining with Mab b3 after passaging the transfected cells. Then, the cells were passaged five times to obtain higher titres of viruses.

Characterization of Recombinant CSFV Viruses Flc30, Flc31, Flc32 and Flc33

Supernatants from SK6c26 cells infected with Flc30, Flc31, Flc32 and Flc33 were used for infection of SK6c26 and SK6 cells. For all viruses approximately 30–50% of the SK6c26 cells were positive by E2 immunoperoxidase staining, four days after infection. For Flc30, Flc31, and Flc33, infection on SK6 cells resulted in only single cells or pairs of single cells expressing E2 and no expression of $E^{ms}$ (FIG. 3). This indicates that infection and replication occurred in the SK6 cells, but that there is no cell-to-cell spread or secondary infection of the mutant viruses.

Supernatant of SK6 cells infected with Flc30, Flc31, or Flc33 was used for infection of new SK6 and SK6c26 cells, but this did not result in infected cells. Thus, the supernatants of these infected SK6 cells did not contain infectious virus (FIG. 3). For the infection of pestiviruses, the interaction of the viral envelope proteins E2 and $E^{ms}$ with the cellular surface is considered to be essential. Due to the absence of $E^{ms}$ in the SK6 cells, no infectious particles could be formed from the viruses Flc30, Flc31, and Flc33.

In contrast, infection with Flc32 derived from supernatants of infected SK6c26 cells showed that 30%–50% of the SK6 cells were infected. Both E2 and $E^{ms}$ could be detected by the E2 and $E^{ms}$ antibodies (FIG. 3). Supernatant of SK6 cells infected with Flc32 can infect new SK6 and SK6c26 cells and thus contains infectious virus (FIG. 3).

This indicated that virus Flc32 is capable to replicate in and to infect SK6 cells. Thus, the recombinant virus with a 405 CYS-SER (Flc32) substitution yields infectious virus, whereas the recombinant viruses with CYS-SER substitutions on position 422 (Flc31) and 381 (Flc33), and a deletion of amino acids 422–436 (Flc30) did not.

These results show an important role for the cysteines at position 422 and 381 for functional activity of $E^{ms}$ as cell-to-cell spread, infectivity, and epitope recognition.

pPRKflc23 for the Expression of Heterologous Proteins pPRKflc23 can be used as vector to incorporate heterologous proteins or fragments of proteins, since the cleavage sites between C-$E^{ms}$ as well as between $E^{ms}$-E1 were left intact. FIG. 7 shows a schematic representation of pPRK-flc23 harbouring the HA epitope, a non-pestivirus sequence. The HA epitope is flanked by the 5 utmost N-terminal amino acids and 6 utmost C-terminal amino acids of $E^{ms}$.

Example 2

Construction and Characterisation of Recombinant CSFV Strains Flc4 and Flc47

Materials and Methods

Cells & Viruses

Swine kidney cells (SK6-M, EP 0 351 901 B1) were grown in Eagle's basal medium containing 5% fetal bovine serum, glutamine (0.3 mg/ml), and the antibiotics penicillin (200 U/ml), streptomycin (0.2 mg/ml), and mycostatin (100 U/ml). Fetal bovine serum was tested for the absence of BVDV and BDV antibodies as described previously (Moormann et al., 1990, Virology 177:184–198).

Recombinant CSFV strain C viruses Flc4 and Flc47 were grown and prepared as described earlier (Moormann et al., 1996, J. Virol. 70: 763–770) with a slight modification; the growth medium of SK6 cells was changed in supplemented Eagle's basal medium. Virus stocks were prepared by passaging the virus five to ten times on SK6b2 cells. The obtained virus titres ranged from 3.54.5 TCID50/ml.

Construction of a Stable SK6 Cell Line Expressing E2

Plasmid pPRb2 contains the E2 gene of CSFV strain Brescia under control of the transcriptional and translation signals of expression vector pEVhisD12 (van Rijn et al., 1992, Vet. Microbiol. 33: 221–230). Plasmid pEVhisD12 is a vector that contains promoter/enhancer sequences of the immediate early gene of the human cytomegalovirus followed by a translation initiation codon and the histidinol dehydrogenase gene (hisD) under control of the SV40 early promoter, which can be used as a selective marker Peeters et al., 1992, J. Virol. 66: 894–905).

For transfection of SK6 cells with pPRb2, lipofectamine (20 µg) (Gibco-BRL) was diluted in 50 µl of Optimem-I (Gibco-BRL) mixed with plasmid DNA (1 µg) diluted in 50 µl Optimem-I (Gibco-BRL) and this mixture was allowed to settle for 15 min at room temperature. SK6 cells grown in 10 cm² tissue culture plates were washed with Optimem-1. Fresh Optimem-I was added (0.5 ml), followed by the DNA transfection mixture. After 20 h of incubation at 37° C., transfected cells were trypsinized and replated in a ten-fold dilution in microtiter plates in medium containing 10 mM histidinol. Medium was replaced every 3–4 days until single colonies were visible. Wells with individual colonies were recloned by limited dilution. Expression of E2 was determined by immunostaining of the cells with Mabs b3 and b4 (Wensvoort et al., 1986, Vet. Microbial. 21: 9–20) directed against conserved epitopes of CSFV E2.

Characterization of the Stable Cell Line SK6b2

E2 expression of the cell line SK6b2 line was tested in an immunoperoxidase staining with E2-specific monoclonal antibodies (Mabs) b3 and b4, (Wensvoort et al., 1986, Vet. Microbiol. 21: 9–20) directed against conserved domain A of CSFV E2 and Mabs b6 and b8 (Wensvoort et al., 1986, Vet. Microbiol. 21: 9–20) directed against domain B and C of Brescia E2.

The amount of E2 was determined by a Ceditest ELISA based on Mab b3 as coating antibody and horseradish peroxidase conjugated Mab b8 as detection antibody as described by Colijn et al., (Vet. Microbiol. 59: 15–25, 1997).

Construction of Full-Length CSFV Constructs Harbouring E2 Deletion Mutants

Figure 8A:
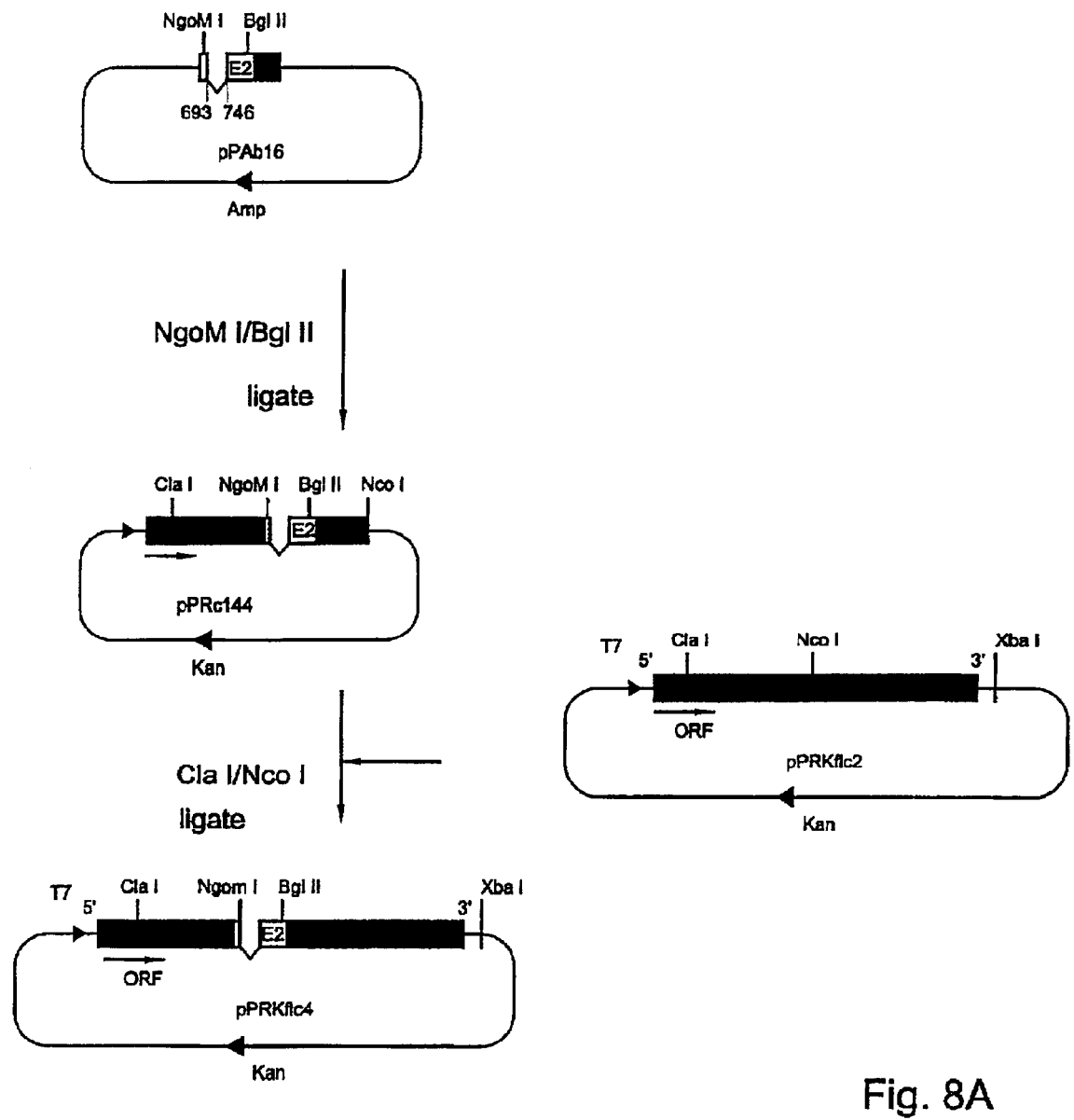

Plasmid pPRKflc4 is a full-length plasmid harbouring a deletion of domain B/C in CSFV-E2 from amino acids 693–746 (FIG. 8A). Therefore, the E2 gene harbouring the deletion from plasmid pPAb16 (van Rijn et al., 1996, J. Gen. Virol. 77: 2737–2745) was inserted in pPRc129 (Moormann et al., 1996, J. Virol. 70: 763–770) by NgoMI/BglII ligation, resulting in plasmid pPRc144. The ClaI/NcoI fragment of pPRc144 was isolated and ligated into the ClaI/NcoI digested vector pPRKflc2, formally named pPRKflc133 (Moormann et al., 1996, J. Virol. 70: 763–770), which resulted in a full-length clone named pPRKflc4.

Figure 8B:
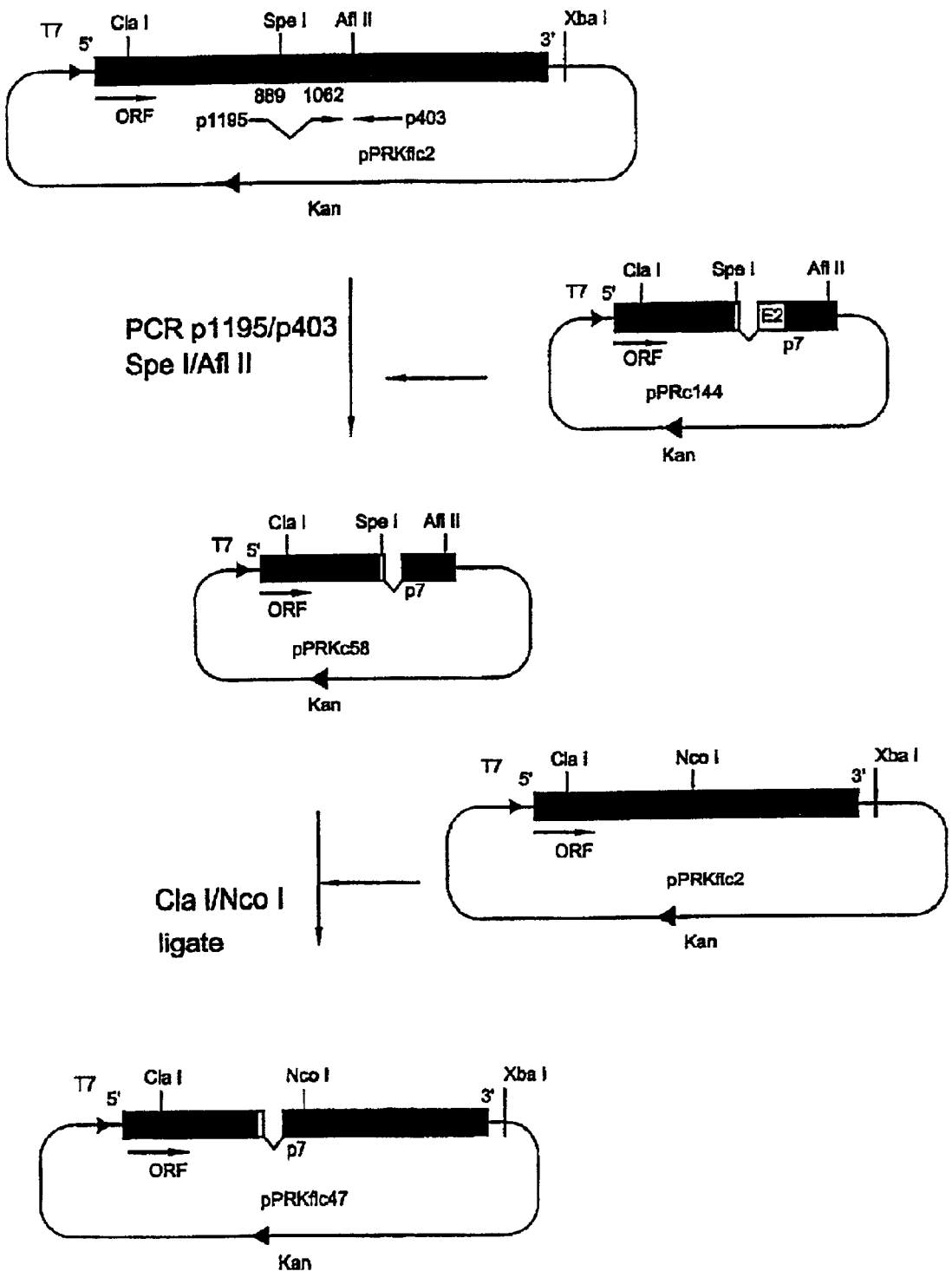

Plasmid pPRKflc47 is a full-length plasmid harbouring a deletion of the complete CSFV-E2 gene from amino acids 689–1062 (FIG. 8B). Therefore, a PCR fragment harbouring the deletion was amplified from plasmid pPRKflc2 with forward primer p1195 (5'-GGC TGT TAC TAG TAA CTG GGG CAC AAG GCT TAC CAT TGG GCC AGG GTG-3' (SEQ ID NO:20)) at position 2412 of the nucleotide sequence of the C-strain and reverse primer p403 (5'-CCC GGG ATC CTC CTC CAG TTT TTT GTA AGT GGA-3' (SEQ ID NO:21)) at nucleotide position 5560. The SpeI/AflII fragment was isolated and ligated in SpeI/AflII-digested pPRc144, resulting in plasmid pPRKc58. The ClaI/NcoI fragment of pPRKc58 was isolated and ligated into the ClaI/NcoI digested vector pPRKflc2, which resulted in full-length clone named pPRKflc47.

Isolation of Recombinant Viruses Flc4 and Flc47

Plasmid DNA from pPRKflc4 and pPRKflc47 was purified on columns (Qiagen) and linearized with XbaI. The DNA was extracted with phenol-chloroform, precipitated with ethanol, and dissolved in water. RNA was transcribed from the linearized plasmid (1 µg) in a 100 µl reaction volume containing 40 mM TrisHCl (pH 7.5), 6 mM MgCl2, 2 mM spermidine, 10 mM dithiothreitol, 40 U rRNAsin (Promega), 0.5 mM each rNTP, and 35 U T7 RNA polymerase (Pharmacia). After 1 h incubation at 37° C., 10 U RNase-free DNaseI (Pharmacia) was added and the mixture was incubated for another 15 min. RNA was extracted with phenol-chloroform, precipitated with ethanol, and dissolved in 10 µl water.

For RNA transfection, 10 µg Lipofectin was diluted in 50 µl of Optimem-I. After a 45 min. incubation at room temperature, 1 µg RNA diluted in 50 µl Optimem-I was added and incubated for an additional 15 min. SK6b2 cells grown in 10 cm$^2$ tissue culture plates were washed with Optimem-I and incubated with the RNA transfection mixture for 4 h at 37° C. Then, the wells were supplied with fresh medium and incubated for 4 days at 37° C. RNA transfection was performed in duplicate. One sample was immunostained with Mab C5 (Wensvoort 1998, Thesis, University of Utrecht) specific for C strain $E^{ms}$. When the $E^{ms}$ immunostaining proved to be positive, the duplicate sample was passaged and split into two samples. One of these samples was used for immunostaining four days after passaging. From wells in which $E^{ms}$ expression was observed, supernatant was applied onto fresh SK6 cells to determine the presence of infectious virus. After four days, the monolayers were fixed and immunostained as described above.

Characterization of Flc4 and Flc47

Viruses were characterized by an immunoperoxidase monolayer assay. For this, SK6 cells were infected with viruses Flc2, Flc4 and Flc47. After incubation for 4 days at 37° C., monolayers were immunostained with Mabs specific for CSFV E2 (Mabs b3/b4) and CSFV $E^{ms}$ Mab C5.

Results

Establishment of an SK6 Cell Line Expressing CSFV E2

SK6 cells were transfected with plasmid pPRb2 containing the CSFV strain Brescia E2 gene and the histidinol (hisD) resistance gene. After 2 weeks, colonies surviving 10 mM histidinol selection were recloned by limited dilution and screened for the expression of E2 by immunostaining the cells with Mab b3 specific for CSFV E2. This clone was named SK6b2. The biochemical properties of the produced E2 of the SK6b2 cell line were characterised. SK6b2 cells reacted with the E2-specific Mabs in an immunoperoxidase assay (Table 4A) and in an indirect ELISA like wild-type E2 (Table 4B). The amount of E2 in the cell lysates of SK6b2 and SK6 cells infected with Flc2 was determined by an indirect ELISA and extrapolated from a standard curve prepared from an immuno-affinity purified preparation of E2 prepared in insect cells. The amount of E2 determined in the SK6b2 cell line (115 ng per cm$^2$) was 3-fold higher than that of SK6 cells infected with Flc2 (30 ng per cm$^2$). The E2 protein of the stable cell line had a similar mobility as the wild-type E2 as determined by SDS-PAGE and was efficiently dimerized like the E2 found in virions (Thiel et al., 1991, J. Virol. 65:4705–4712) (Table 4B).

Construction and Recovery of C Strain CSFV E2 Recombinant Viruses

Previous studies have shown that E2 consists of the two antigenic units A and B/C and that the separate antigenic units of E2 can protect pigs against classical swine fever (van Rijn et al., 1996, J. Gen. Virol. 77: 2737–2745). Therefore, two deletion mutants were constructed: plasmid pPRKflc4, which possesses a deletion in E2 of domain B/C between amino acids 693–746 and pPRKflc47, in which the entire E2 gene between amino acids 689–1062 was deleted. FIGS. 8A, 8B show a schematic representation of the construction of these recombinant E2 full-length clones.

RNA transcribed from the linearized full-length cDNA, was transfected into the SK6b2 cell line expressing E2. The cells were positive after immunostaining with Mab C5. Then, the transfected cells were passaged to obtain higher titres of viruses. Supernatants isolated from serial passages contained infectious viruses. Between five to ten passages were required to obtain a virus titre of approximately 3.54.5 TCID50/ml and this stock was used for further characterisation of the viruses.

Characterisation of Recombinant E2 CSFV Viruses

Supernatants from the SK6b2 cells were used for infection of SK6 and SK6b2 cells to characterize Flc4 and Flc47. Four days after infection, approximately 30–50% of the SK6b2 cells were positive by $E^{ms}$ immunoperoxidase staining.

Infection on SK6 cells resulted in only single cells or pairs of single cells expressing $E^{ms}$ four days after infection. This indicates that infection and replication occurred in the SK6 cells, but that there is no cell-to-cell spread or secondary infection of the recombinant viruses.

Supernatant of the Flc4- and Flc47-infected SK6 cells were used for infection of new SK6 and SK6b2 cells, but this did not result into infected cells. Thus, the supernatants of these infected SK6 cells do not contain infectious virus (Table 5). For the infection of pestiviruses, the interaction of the viral envelope proteins E2 and $E^{ms}$ with the cell surface are considered to be essential. Due to the absence of E2 in the SK6 cells, no infectious particles could be formed. Infection of SK6 cells with Flc2 from infected SK6b2 cells resulted in a positive immunoperoxidase staining for E2 and $E^{ms}$ and in secondary infection of the virus.

SK6 cells infected with the viruses Flc4 and Flc47 could be immunostained with Mab C5 directed against $E^{ms}$, whereas only Flc4 and Flc2 reacted with Mab b3, directed against the A domain of CSFV E2 (Table 5). As expected, Flc47 was completely negative for the Mabs against the A, B and C domains (Table 5).

Transfection of in vitro RNA derived from pPRKflc4 and pPRKflc47 into the SK6-cell line resulted in transient expression of $E^{ms}$, but passaging the transfected cells six times did not result in the recovery of recombinant viruses. This indicated that the recombinant E2 viruses Flc4 and Flc47 require complementation of E2 to obtain infectious virus.

Example 3

Animal Experiment: 298-47042-00/98-06

Pigs Vaccinated with Flc22 and Flc23 are Protected Against a Lethal Challenge with Virulent CSFV Strain Brescia
Materials and Methods
Animals Pigs of 6–7 weeks of age from conventional sows were obtained. Pigs were randomly divided in groups and housed in separate stables of the highly containment facilities of ID-DLO. The animals were fed once a day, in a trough, with complete food pellets, and could drink water from a nipple ad libitum.
Vaccination and Challenge The pigs were divided into two groups of 2 pigs. The pigs in group A were vaccinated with strain Flc23; the pigs in group B were vaccinated with strain Flc22. The pigs were vaccinated via several routes of inoculation. The pigs were sedated and placed on their backs before inoculation with a virus suspension (2 ml containing 105 TCID50/ml) which was instilled dropwise into the nostrils. In addition, two milliliters of virus suspension was inoculated intravenously, 2 ml of virus was inoculated intradermally. The vaccines were emulsified in a water-oil-water adjuvant (Hulst et al., 1993, J. Virol. 67:5435–5442), and 2 ml of this vaccine was inoculated intramuscularly in the neck behind the ears. In total, each pig received 8 ml of vaccine, corresponding with $8 \times 10^5$ $TCID_{50}$/ml.

The pigs were challenged intranasally with 100 50% lethal doses (=100 $LD_{50}$) of CSFV strain Brescia 456610 (Terpstra and Wensvoort, 1988, Vet. Microbiol. 16:123–128) four weeks after vaccination. Viral contents of the vaccine inoculum were determined by titration of a sample taken after return from the stable. The pigs were euthanized 7 weeks after challenge.
Clinical Observation The pigs were checked daily by the animal technicians, abnormal findings were recorded and if necessary the supervising veterinarian was called. Each group was observed at least 15 minutes per day before and during feeding and cleansing of the stable. A reduction in food uptake of the group or an individual animal was noted. Body temperatures were recorded during several days before and up to 20 days after challenge.
Blood Analysis After Challenge EDTA-blood samples were collected on days 1, 2, 6, 9, 12 and 15 after challenge to monitor changes of leukocyte and thrombocyte numbers in the blood. A decrease in the number of leukocytes (leucopenia) and thrombocytes (thrombocytopenia) is one of the typical signs of CSF. Normal cell counts for white blood cells and thrombocytes in conventional swine range between 11–23 109/l and 320–720 109/l, respectively. Both ranges mentioned vary in each pig. The blood cell analyses were performed with a Medonic CA 570 coulter counter. Leucopenia and thrombocytopenia were defined as cell/platelets counts considerably lower than the minimum number mentioned above, preferably for more than one day.
Virus Isolation and Viral Antigen Detection Virus isolation: Peripheral blood leukocytes were extracted from EDTA-blood samples taken on day —1, 2, 6, 9, 12 and 15 after challenge to monitor viraemia. The samples were stored at –70° C. The presence of CSFV in the leukocytes was examined as follows. In an M24 plate (Greiner), 300 µl (containing approximately 5×106 cells) of a swine kidney cell (SK6) suspension was added to each well and cultured at 37° C. and 5% $CO_2$ in a humid chamber for 24 h. After 24 h, the medium was removed and 300 µl of an undiluted freeze/thawed leukocyte sample was added per well. After one hour of incubation at 37° C. and 5% $CO_2$, the sample was removed. The monolayer was then washed by adding and removing 400 µl of culture medium (Eagle basal medium). Subsequently, 800 µl of culture medium (Eagle basal medium with 5% fetal bovine serum (FBS), free of pestivirus antibodies, and 1% of an antibiotic stock containing glutamine (0.3 mg ml$^{-1}$), penicillin (200 units ml$^{-1}$), streptomycin (0.2 mg ml$^{-1}$) and mycostatin (100 U ml$^{-1}$)) was added per well. After four days, the monolayers were washed in 10% NaCl solution, dried for 1 h at 800 C., incubated with a buffered solution containing CSFV-specific conjugated antibodies, washed and stained. The monolayers were read microscopically for stained cells. Results were expressed as positive or negative for virus.

IFT: At post-mortem, tissue samples were collected from tonsil, spleen, kidney, and ileum, and were tested by direct immunofluorescent technique (Ressang and De Boer, 1967, Tijdschrift voor Diergeneeskunde 92:567–586) for the presence of viral antigen. Cryostat sections (4 µm thick, two per organ) from these tissue samples were fixed and incubated with a polyclonal swine anti-pestivirus FITC-conjugated serum. After washing, the sections were read under a fluorescence microscope. Results were expressed as positive (=fluorescence) or negative (=no fluorescence).
Serological Response Serum blood samples of all pigs except the controls were collected at one week intervals after challenge during 6 weeks. Samples were stored at –20° C. and assayed in a CSFV-specific (Terpstra and Wensvoort, 1984, Vet. Microbiol. 33:113–120) virus neutralisation test (NPLA), in the Ceditest ELISA for detecting CSFV-specific antibodies against E2 (Colijn et al., 1997, Vet. Microbiol. 59:15–25), and in a Ceditest ELISA for the detection of antibodies against $E^{ms}$ (de Smit et al., in prep).

CSFV-specific neutralising antibody titres in serum were determined in a microtiter system. Serial two-fold dilutions of serum were mixed with an equal volume of a CSFV (strain Brescia) suspension which contained 30–300 TCID50. After incubation for 1 hour at 37° C. in a $CO_2$ incubator approximately 25,000 PK-15 cells per well were added. After four days, the microtiter plates were treated as mentioned above and read microscopically. The CSFV neutralising titre was expressed as the reciprocal of the highest dilution that neutralised all viruses.

The CSFV E2-ELISA was performed according to the instructions of the manufacturer (Colijn et al., 1997, ibid.). The CSFV $E^{ms}$-ELISA was performed as follows. Test sera (30 µl) are pre-incubated with CSFV $E^{ms}$-antigen (70 µl of a working dilution of baculovirus expressed $E^{ms}$ of CSFV strain Brescia) in a 96-well non-coated microtiter plate containing 45 µl of ELISA buffer for 30 min at 37° C. Thereafter, 50 µl of this pre-incubation mix is added to a microtiter plate coated with the $E^{ms}$-specific monoclonal antibody 137.5, and containing 50 µl of a working solution of the horseradish peroxidase conjugated $E^{RNS}$-specific monoclonal antibody 140.1.1. The plates are incubated for 1 h at 37° C., washed six times with 200 µl of washing solution, and incubated for 30 min at room temperature with 100 µl of a ready-to-use chromogen(3,3',5,5'-tetramethylbenzidine)/substrate solution. The color reaction is stopped by adding 100 µl of a 0.5 M H2SO4 solution, and the optical density was measured at 450 nm using an Easy Reader spectrophotometer (SLT Vienna).

Results

Clinical Observation, Viral Antigen Detection, Leukocyte/Thrombocyte Counts

After vaccination, none of the animals developed clinical signs or fever (Table 6). Both group A and B pigs developed a mild fever (40° C.<T<41° C.) for three days, starting 3 days after challenge. None of the vaccinated pigs, either in group A (Flc23) or B (Flc22) developed leucopenia or thrombocytopenia (Table 6), although six days after challenge a slight drop in the thrombocyte count and leukocyte count was observed for most of the pigs. In both groups A and B, no virus was detected in the leukocytes. Moreover, the organs of all pigs were IFT-negative at the end of the experiment, indicating the absence of persistent infections.

Serological Response

After vaccination of the pigs in group A (Flc23) and group B (Flc22), no CSFV-specific antibodies were detected with the E2-ELISA (Table 7) and the $E^{ms}$ ELISA (Table 8). This finding was consistent with the NPLA results: all vaccinated pigs remained negative for neutralising antibodies against CSFV (Table 9).

After challenge inoculation, maximum inhibition percentages were observed in the E2-ELISA in all inoculated pigs. Also, all four pigs seroconverted in the $E^{ms}$ ELISA. In the neutralising antibody assays, all inoculated pigs showed high titres against CSFV. These results clearly show that both Flc22 and Flc23 vaccines protect against a lethal challenge of virulent Brescia, and can be discriminated from infected animals by CSFV-specific $E^{ms}$-ELISA.

TABLE 1

IPMA on SK6 monolayers transfected with $E^{ms}$ expression plasmids harbouring the nucleotide sequence of the autoprotease and structural genes (Npro —C-recombinant $E^{ms}$-E1-E2)

| Plasmid | Deletion* | $E^{ms}$ | | | | E2 | |
| --- | --- | --- | --- | --- | --- | --- | --- |
| | | C5 | 140.1 | R 716 | 137.5 | b3 | b4 |
| pPRK83 | None | + | + | + | + | + | + |
| pPRKc49 | 436 to 488 | + | + | + | + | + | + |
| pPRKc50 | 422 to 488 | − | − | − | − | + | + |
| pPRKc51 | 422 to 436 | − | − | − | − | + | + |
| PPRKc48 | 272 to 488 | − | − | − | − | + | + |

*amino acid numbering of CSFV strain C (Moormann et al., 1996, J. Virol. 70: 763–770)

TABLE 2A

IPMA reactivity of the SK6c26 and SK6 cells with CSFV $E^{ms}$ antibodies

| | CSFV antibodies | | | |
| --- | --- | --- | --- | --- |
| Cells | Mab C5 | Mab 140.1 | Mab 137.5 | R 716 |
| SK6c26 | + | + | + | + |
| SK6 | − | − | − | − |

TABLE 2B

Comparison of $E^{ms}$ of SK6c26 and SK6 infected cells with Flc2

| Cells | ng $E^{ms}.cm^{-2a}$ | RNase activity $(A_{260}.min^{-1}.mg^{-1})^b$ | Dimerization$^c$ |
| --- | --- | --- | --- |
| SK6c26 | 10 | 130 | + |
| SK6 | <0.1 | 0 | − |
| SK6 Flc2 infected | 30 | 171 | + |

$^a$The amount of $E^{ms}$ in the cell lysates per cm² was extrapolated from a standard curve prepared from an immuno-affinity purified preparation of $E^{ms}$ produced in insect cells.
$^b$The RNase activity was determined as $A_{260}$ units per mg $E^{ms}$ per min as described by Hulst et al., 1998, J. Virol. 72:151–157.
$^c$detection of dimers of $E^{ms}$ by nonreducing SDS-PAGE

TABLE 3

Neutralization of CSF viruses by antibodies

| | Virus neutralizing reduction (log $TCID_{50}$/ml) with serum$^a$ | |
| --- | --- | --- |
| Virus | 716 (directed against $E^{ms}$)$^b$ | 539 (directed against E2)$^c$ |
| Flc2 | −3.0 | −1.75 |
| Flc22 | −3.0 | −1.75 |
| Flc23 | −3.25 | −1.0 |

$^a$Log $TCID_{50}$/ml reduction of CSFV titers due to the presence of serum
$^b$rabbit serum prepared against $E^{ms}$ of CSFV strain C
$^c$pig serum specifically directed against E2 of CSFV strain Brescia

TABLE 4A

Reactivity of SK6b2 and SK6 cells with CSFV E2 Mabs

| | Reactivity of CSFV antibodies in IPMA | | |
| --- | --- | --- | --- |
| Cells | b3 | b8 | b6 |
| SK6b2 | + | + | + |
| SK6 | − | − | − |

TABLE 4B

Characterization of the SK6b2 cell line

| Cells | Dimerization$^a$ | ng $E2.cm^{-2b}$ |
| --- | --- | --- |
| SK6b2 | + | 115 |
| SK6 | − | 0 |
| SK6Flc2 infected | + | 38 |

$^a$Dimerization of E2 was determined on SDS-PAGE under nonreducing conditions
$^b$The amount of E2 in the cell lysates per cm² as measured in the E2 ELISA was extrapolated from a standard curve prepared from an immuno-affinity purified preparation of E2 produced in insect cells.

TABLE 5

Characterization of recombinant E2 viruses on SK6 cells

| Virus | IPMA reactivity on SK6 cells | | | Infectious virus recovered[a] | |
|---|---|---|---|---|---|
| | C5 | b3 | b6 | SK6b2 cells | SK6 cells |
| Flc2 | + | + | + | + | + |
| Flc4 (deletion B/C domains of E2) | + | + | − | + | − |
| Flc47 (deletion E2) | + | − | − | + | − |

[a]Infectious virus is recovered if supernatants of infected cells can infect new SK6 and SK6b2 cells.
Spread of virus via cell-to-cell spread and spread of virus due to division of cells is not considered due to infection of virus.

TABLE 6

Results of virus isolation, cytopenia and fever after challenge with CSFV

| Group | pig no. | # days with fever[a] | Viremia | IFT | Cytopenia[b] | death |
|---|---|---|---|---|---|---|
| A | 469 | 3 | − | − | − | − |
| Flc23 | 476 | 5 | − | − | − | − |
| B | 477 | 5 | − | − | − | − |
| Flc22 | 478 | 6 | − | − | − | − |

[a]Fever: body temperature >40° C.
[b]Cytopenia: thrombocytopenia and/or leucopenia

TABLE 7

Results of the Ceditest ® ELISA for the detection of CSFV-E2 antibodies[a]

| Group | Animal | days post challenge | | | | | | | | |
|---|---|---|---|---|---|---|---|---|---|---|
| A | 469 | 0 | 0 | 27 | 34 | 17 | 61 | 100 | 100 | 100 |
|   | 476 | 0 | 0 | 0 | 0 | 18 | 97 | 100 | 100 | 100 |
| B | 477 | 0 | 0 | 11 | 17 | 32 | 93 | 100 | 100 | 100 |
|   | 478 | 0 | 0 | 15 | 24 | 34 | 51 | 100 | 100 | 100 |

[a]The Ceditest ® E2-ELISA specifically detects antibodies against envelope protein E2 of CSFV. Test results are expressed as the percentage inhibition of a standard signal; <30% is negative, 30–50% inhibition is doubtful, >50% inhibition is positive.

TABLE 8

Results of the Ceditest ® ELISA for the detection of CSFV-E$^{ms}$ antibodies[a]

| Group | Animal no. | days post challenge | | | | | | | | |
|---|---|---|---|---|---|---|---|---|---|---|
| | | −28 | −15 | −1 | 6 | 12 | 19 | 27 | 33 | 49 |
| A. Flc23 | 469 | 17 | 29 | 26 | 22 | 76 | 80 | 81 | 74 | 83 |
|   | 476 | 15 | 28 | 25 | 14 | 70 | 76 | 81 | 69 | 79 |
| B Flc22 | 477 | 13 | 30 | 13 | 20 | 70 | 54 | 49 | 50 | 62 |
|   | 478 | 12 | 34 | 35 | 22 | 68 | 84 | 81 | 87 | 92 |

[a]The Ceditest ® E$^{ms}$-ELISA specifically detects antibodies against envelope protein E$^{ms}$ of CSFV. The test results are expressed as the percentage inhibition of a standard signal; <50% is negative, =50% is positive

TABLE 9

Results of the NPLA for the detection of CSFV Brescia-specific neutralizing antibodies

| Group | Animal No. | Days post challenge | | | | | | | | | |
|---|---|---|---|---|---|---|---|---|---|---|---|
| | | −28 | −21 | −15 | −9 | −1 | 6 | 12 | 19 | 27 | 33 | 49 |
| A | 469 | <10 | <10 | <10 | <10 | 15 | 80 | >1280 | >1280 | >1280 | >1280 | 7680 |
| Flc23 | 476 | <10 | <10 | <10 | <10 | <10 | 80 | >1280 | >1280 | >1280 | >1280 | 7680 |
| B | 477 | <10 | <10 | <10 | <10 | 10 | 80 | >1280 | >1280 | >1280 | >1280 | >20480 |
| Flc22 | 478 | <10 | <10 | <10 | <10 | <10 | 480 | >1280 | >1280 | >1280 | >1280 | 7680 |

What is claimed is:

1. A recombinant nucleic acid that, upon inoculation of an animal, can elicit an immune response directed against immunodominant parts of structural proteins of a pestivirus without having the ability to spread through the inoculated animal, said recombinant nucleic acid comprising a genome of a pestivirus encoding at least one structural protein or an immunodominant part thereof, said genome having a functional deletion in a sequence encoding at least one protein related to viral spread.

2. A cell permissive for pestivirus infection comprising:
a nucleic acid construct encoding at least one pestiviral protein or substantial part thereof related to viral spread; and
a pestiviral genome containing a defect complemented by said construct;
wherein said cell allows for packaging of said genome and pestiviral protein or substantial part thereof in a pestivirus-like particle.

3. The cell of claim 2, wherein said at least one pestiviral protein or substantial part thereof related to viral spread is stably expressed.

4. A process of making pestivirus-like particles comprising:
transfecting a cell with a recombinant nucleic acid comprising a pestiviral genome having a functional deletion in a sequence encoding at least one pestiviral protein related to viral spread, said genome being capable of RNA replication in a suitable cell and encoding at least one structural protein of pestivirus or at least one immunodominant part thereof,
wherein said cell comprises a second nucleic acid construct encoding at least one pestiviral protein or a substantial part thereof related to viral spread and allowing packaging of said recombinant pestiviral genome in a pestivirus-like particle;
allowing said pestiviral genome to replicate in said cell;
allowing the replicated recombinant pestiviral genome to package into a pestivirus-like particle comprising the protein encoded by the second nucleic acid; and
harvesting said pestivirus-like particles.

5. The process according to claim 4 wherein the second nucleic acid construct encoding the at least one pestiviral protein or substantial part thereof related to viral spread is stably expressed.

6. A process of making a vaccine comprising:
transfecting a cell with a recombinant nucleic acid comprising a pestiviral genome having a functional deletion in a sequence encoding at least one pestiviral protein related to viral spread, said genome being capable of RNA replication in a suitable cell and encoding at least one structural protein of pestivirus or at least one immunodominant part thereof;
wherein said cell comprises a second nucleic acid construct encoding at least one pestiviral protein or a substantial part thereof related to viral spread and allowing packaging of said recombinant pestiviral genome in a pestivirus-like particle;
allowing said pestiviral genome to replicate in said cell;
allowing the replicated recombinant pestiviral genome to package into a pestivirus-like particle comprising the protein encoded by the second nucleic acid;
harvesting said pestivirus-like particles; and
preparing a suspension of said pestivirus-like particles in a suitable diluent.

7. The process according to claim 6 comprising combining said suspension with an adjuvant.

8. The process according to claim 6, wherein said functional deletion in the sequences encoding at least one structural protein or pestivirus or at least one immunodominant part thereof comprises a functional deletion in $E^2$ or $E^{rns}$.

* * * * *

UNITED STATES PATENT AND TRADEMARK OFFICE
CERTIFICATE OF CORRECTION

PATENT NO.       : 6,923,969 B2                                          Page 1 of 1
APPLICATION NO.  : 09/948966
DATED            : August 2, 2005
INVENTOR(S)      : Myra N. Widjojoatmodjo et al.

It is certified that error appears in the above-identified patent and that said Letters Patent is hereby corrected as shown below:

| | |
|---|---|
| COLUMN 10, LINE 36, | change "GCA TAT GTA CCC TAT TIT GCT TG 3'" to --GCA TAT GTA CCC TAT TTT GCT TG 3'-- |
| COLUMN 11, LINE 24, | change "(5'CCG AAA" to --(5' CCG AAA-- |
| COLUMN 11, LINE 26, | change "(5'CAT AAG" to --(5' CAT AAG-- |
| COLUMN 11, LINES 42,43 | change "p1124 '5 GAC AGA TCT ATC GAT TAC CCA TAC GAT GTT CCA GAT 3' (SEQ ID NO:7)" to --p1124 '5 GAC AGA TCT ATC GAT <u>TAC CCA TAC GAT GTT CCA GAT</u> 3' (SEQ ID NO:7)-- |
| COLUMN 11, LINES 43,44 | change "p1255 5'GAC GTC GAC GGA TCC AGC GTA ATC TGG AAC ATC 3' (SEQ ID NO:8)" to --p1255 5' GAC GTC GAC GGA TCC <u>AGC GTA ATC TGG AAC ATC</u> 3' (SEQ ID NO:8)-- |
| COLUMN 11, LINE 56, | change "(5'CCG AAA" to --(5' CCG AAA-- |
| COLUMN 11, LINE 57, | change "(5'CAT AAG" to --(5' CAT AAG-- |
| COLUMN 12, LINE 24, | change "atamino" to --at amino-- |
| COLUMN 12, LINE 35, | change "(5'CCT GAC" to --(5' CCT GAC-- |

Signed and Sealed this

Sixteenth Day of December, 2008

JON W. DUDAS
*Director of the United States Patent and Trademark Office*

SEQUENCE LISTING

<160> NUMBER OF SEQ ID NOS: 25

<210> SEQ ID NO 1
<211> LENGTH: 30
<212> TYPE: DNA
<213> ORGANISM: Pestivirus sp.
<220> FEATURE:
<221> NAME/KEY: primer_bind
<222> LOCATION: (1)..(30)
<223> OTHER INFORMATION: PCR primer p974

<400> SEQUENCE: 1
aagaaaagat ctaaagccct attggcatgg       30

-continued

<210> SEQ ID NO 2
<211> LENGTH: 34
<212> TYPE: DNA
<213> ORGANISM: Pestivirus sp.
<220> FEATURE:
<221> NAME/KEY: primer_bind
<222> LOCATION: (1)..(34)
<223> OTHER INFORMATION: PCR primer p976

<400> SEQUENCE: 2
ttgttacagc tgcatatgta ccctattttg cttg 34

<210> SEQ ID NO 3
<211> LENGTH: 33
<212> TYPE: DNA
<213> ORGANISM: Pestivirus sp.
<220> FEATURE:
<221> NAME/KEY: primer_bind
<222> LOCATION: (1)..(33)
<223> OTHER INFORMATION: forward oligomer p1135

<400> SEQUENCE: 3
ccgaaaatat aactcaatgg tttggcgctt atg 33

<210> SEQ ID NO 4
<211> LENGTH: 33
<212> TYPE: DNA
<213> ORGANISM: Pestivirus sp.
<220> FEATURE:
<221> NAME/KEY: primer_bind
<222> LOCATION: (1)..(33)
<223> OTHER INFORMATION: reverse oligomer p1136

<400> SEQUENCE: 4
cataagcgcc aaaccattga gttatatttt cgg 33

<210> SEQ ID NO 5
<211> LENGTH: 48
<212> TYPE: DNA
<213> ORGANISM: Pestivirus sp.
<220> FEATURE:
<221> NAME/KEY: primer_bind
<222> LOCATION: (1)..(48)
<223> OTHER INFORMATION: PCR reverse primer p1120

<400> SEQUENCE: 5
gacggattcg gcataggcgc caaaccatgg gctctctata actgtaac 48

<210> SEQ ID NO 6
<211> LENGTH: 9
<212> TYPE: PRT
<213> ORGANISM: Pestivirus sp.
<220> FEATURE:
<221> NAME/KEY: MUTAGEN
<222> LOCATION: (1)..(9)
<223> OTHER INFORMATION: HA epitope, amino acid sequence

<400> SEQUENCE: 6

Tyr Pro Tyr Asp Val Pro Asp Tyr Ala
1 5

<210> SEQ ID NO 7
<211> LENGTH: 36
<212> TYPE: DNA
<213> ORGANISM: Pestivirus sp.
<220> FEATURE:
<221> NAME/KEY: misc_feature
<223> OTHER INFORMATION: Includes HA epitope sequence at nucleotides 16-
33.

-continued

<220> FEATURE:
<221> NAME/KEY: primer_bind
<222> LOCATION: (1)..(36)
<223> OTHER INFORMATION: PCR primer p1124

<400> SEQUENCE: 7
gacagatcta tcgattaccc atacgatgtt ccagat 36

<210> SEQ ID NO 8
<211> LENGTH: 33
<212> TYPE: DNA
<213> ORGANISM: Pestivirus sp.
<220> FEATURE:
<221> NAME/KEY: misc_feature
<223> OTHER INFORMATION: Includes HA epitope sequence at nucleotides 16-33.
<220> FEATURE:
<221> NAME/KEY: primer_bind
<222> LOCATION: (1)..(33)
<223> OTHER INFORMATION: PCR primer p1125

<400> SEQUENCE: 8
gacgtcgacg gatccagcgt aatctggaac atc 33

<210> SEQ ID NO 9
<211> LENGTH: 20
<212> TYPE: DNA
<213> ORGANISM: Pestivirus sp.
<220> FEATURE:
<221> NAME/KEY: primer_bind
<222> LOCATION: (1)..(20)
<223> OTHER INFORMATION: PCR forward primer p935

<400> SEQUENCE: 9
ccgaaaatat aactcaatgg 20

<210> SEQ ID NO 10
<211> LENGTH: 20
<212> TYPE: DNA
<213> ORGANISM: Pestivirus sp.
<220> FEATURE:
<221> NAME/KEY: primer_bind
<222> LOCATION: (1)..(20)
<223> OTHER INFORMATION: PCR reverse primer p925

<400> SEQUENCE: 10
cataagcgcc aaaccaggtt 20

<210> SEQ ID NO 11
<211> LENGTH: 48
<212> TYPE: DNA
<213> ORGANISM: Pestivirus sp.
<220> FEATURE:
<221> NAME/KEY: primer_bind
<222> LOCATION: (1)..(48)
<223> OTHER INFORMATION: PCR reverse primer p1121

<400> SEQUENCE: 11
gacggattcg gcataggcgc caaaccaatc cccatacaag gtatcctc 48

<210> SEQ ID NO 12
<211> LENGTH: 36
<212> TYPE: DNA
<213> ORGANISM: Pestivirus sp.
<220> FEATURE:
<221> NAME/KEY: primer_bind
<222> LOCATION: (1)..(36)
<223> OTHER INFORMATION: PCR primer p1147

-continued

```
<400> SEQUENCE: 12
caaactgccg cactcatgtg ggctctctat aactgt                        36

<210> SEQ ID NO 13
<211> LENGTH: 23
<212> TYPE: DNA
<213> ORGANISM: Pestivirus sp.
<220> FEATURE:
<221> NAME/KEY: primer_bind
<222> LOCATION: (1)..(23)
<223> OTHER INFORMATION: PCR forward primer p1140

<400> SEQUENCE: 13
gagagccctt cgaatttcaa tgt                                      23

<210> SEQ ID NO 14
<211> LENGTH: 24
<212> TYPE: DNA
<213> ORGANISM: Pestivirus sp.
<220> FEATURE:
<221> NAME/KEY: primer_bind
<222> LOCATION: (1)..(24)
<223> OTHER INFORMATION: PCR forward primer p1148

<400> SEQUENCE: 14
cctgaccggt tcgaagaaag ggaa                                     24

<210> SEQ ID NO 15
<211> LENGTH: 27
<212> TYPE: DNA
<213> ORGANISM: Pestivirus sp.
<220> FEATURE:
<221> NAME/KEY: primer_bind
<222> LOCATION: (1)..(27)
<223> OTHER INFORMATION: PCR forward primer p1149

<400> SEQUENCE: 15
tgcgctgtga ctagtaggta cgataaa                                  27

<210> SEQ ID NO 16
<211> LENGTH: 21
<212> TYPE: DNA
<213> ORGANISM: Pestivirus sp.
<220> FEATURE:
<221> NAME/KEY: primer_bind
<222> LOCATION: (1)..(21)
<223> OTHER INFORMATION: PCR primer p1154

<400> SEQUENCE: 16
gttaccagtt gttctgatga t                                        21

<210> SEQ ID NO 17
<211> LENGTH: 21
<212> TYPE: DNA
<213> ORGANISM: Pestivirus sp.
<220> FEATURE:
<221> NAME/KEY: primer_bind
<222> LOCATION: (1)..(21)
<223> OTHER INFORMATION: PCR primer p305

<400> SEQUENCE: 17
ggggtgcagt tgttgtatcc a                                        21

<210> SEQ ID NO 18
<211> LENGTH: 20
<212> TYPE: DNA
<213> ORGANISM: Pestivirus sp.
```

-continued

```
<220> FEATURE:
<221> NAME/KEY: primer_bind
<222> LOCATION: (1)..(20)
<223> OTHER INFORMATION: P -continued

```
Gly Thr Asn Tyr Thr Cys Cys Lys Leu Gln Arg Phe Thr His Glu Trp
65                  70                  75                  80

Asn Lys His Gly Trp Cys Asn Trp His Asn Ile Asp Pro Trp Ile Gln
                85                  90                  95

Leu Met Asn Arg Thr Gln Ala Asp Leu Ala Glu Gly Pro Pro Val Lys
            100                 105                 110

Glu Cys Ala Val Thr Cys Arg Tyr Asp Lys Asp Ala Asp Ile Asn Val
            115                 120                 125

Val Thr Gln Ala Arg Asn Arg Pro Phe Thr Thr Leu Thr Gly Cys
        130                 135                 140

Lys Lys Gly Lys Asn Phe Ser Phe Ala Gly Thr Val Ile Glu Ser Pro
145                 150                 155                 160

Cys Asn Phe Asn Val Ser Val Glu Asp Thr Leu Tyr Gly Asp His Glu
                165                 170                 175

Cys Gly Ser Leu Leu Gln Asp Ala Ala Leu Tyr Leu Val Asp Gly Met
            180                 185                 190

Thr Asn Thr Ile Glu Phe Thr Asn Ala Arg Gln Gly Ala Ala Arg Val
            195                 200                 205

Thr Ser Trp Leu Gly Arg Gln Leu Arg Thr Ala Gly Lys Arg Leu Glu
        210                 215                 220

Gly Arg Ser Lys Thr Trp Phe Gly Ala Tyr Ala
225                 230                 235
```

<210> SEQ ID NO 23
<211> LENGTH: 166
<212> TYPE: PRT
<213> ORGANISM: Pestivirus sp.
<220> FEATURE:
<221> NAME/KEY: MUTAGEN
<222> LOCATION: (1)..(166)
<223> OTHER INFORMATION: Erns amino acid sequence of Flc22

<400> SEQUENCE: 23

```
Glu Asn Ile Thr Gln Trp Asn Leu Ser Asp Asn Gly Thr Asn Phe Thr
1               5                   10                  15

Gly Ile Gln His Ala Met Tyr Leu Arg Gly Val Asn Arg Ser Leu His
            20                  25                  30

Gly Ile Trp Pro Gly Lys Ile Cys Lys Gly Val Pro Thr His Leu Ala
        35                  40                  45

Thr Asp Val Glu Leu Lys Glu Ile Gln Gly Met Met Asp Ala Ser Glu
    50                  55                  60

Gly Thr Asn Tyr Thr Cys Cys Lys Leu Gln Arg Phe Thr His Glu Trp
65                  70                  75                  80

Asn Lys His Gly Trp Cys Asn Trp His Asn Ile Asp Pro Trp Ile Gln
                85                  90                  95

Leu Met Asn Arg Thr Gln Ala Asp Leu Ala Glu Gly Pro Pro Val Lys
            100                 105                 110

Glu Cys Ala Val Thr Cys Arg Tyr Asp Lys Asp Ala Asp Ile Asn Val
            115                 120                 125

Val Thr Gln Ala Arg Asn Arg Pro Phe Thr Thr Leu Thr Gly Cys
        130                 135                 140

Lys Lys Gly Lys Asn Phe Ser Phe Ala Gly Thr Val Ile Glu Ser Pro
145                 150                 155                 160

Trp Phe Gly Ala Tyr Ala
                165
```

```
-continued

<210> SEQ ID NO 24
<211> LENGTH: 11
<212> TYPE: PRT
<213> ORGANISM: Pestivirus sp.
<220> FEATURE:
<221> NAME/KEY: MUTAGEN
<222> LOCATION: (1)..(11)
<223> OTHER INFORMATION: Erns amino acid sequence of Flc23

<400> SEQUENCE: 24

Glu Asn Ile Thr Gln Trp Phe Gly Ala Tyr Ala
1               5                   10

<210> SEQ ID NO 25
<211> LENGTH: 20
<212> TYPE: PRT
<213> ORGANISM: Pestivirus sp.
<220> FEATURE:
<221> NAME/KEY: MUTAGEN
<222> LOCATION: (1)..(20)
<223> OTHER INFORMATION: HA epitope in pPRKflc23

<400> SEQUENCE: 25

Glu Asn Ile Thr Gln Tyr Pro Tyr Asp Val Pro Asp Tyr Ala Trp Phe
1               5                   10                  15

Gly Ala Tyr Ala
            20
```